United States Patent
Yang et al.

(10) Patent No.: US 8,603,806 B2
(45) Date of Patent: Dec. 10, 2013

(54) MATERIALS AND METHODS FOR CELL-BASED ASSAYS

(75) Inventors: Shang-Tian Yang, Dublin, OH (US); Xudong Zhang, Columbus, OH (US); Yuan Wen, Dublin, OH (US)

(73) Assignee: The Ohio State Universtiy Research Foundation, Columbus, OH (US)

( * ) Notice: Subject to any disclaimer, the term of this patent is extended or adjusted under 35 U.S.C. 154(b) by 944 days.

(21) Appl. No.: 11/556,132

(22) Filed: Nov. 2, 2006

(65) Prior Publication Data
US 2007/0099294 A1  May 3, 2007

Related U.S. Application Data

(60) Provisional application No. 60/732,820, filed on Nov. 2, 2005, provisional application No. 60/732,821, filed on Nov. 2, 2005.

(51) Int. Cl.
  *C12M 1/22* (2006.01)
  *C12M 3/00* (2006.01)
(52) U.S. Cl.
  USPC ............ 435/305.2; 435/287.1; 435/288.2; 435/288.4; 435/288.7; 435/304.3; 435/305.1; 435/808
(58) Field of Classification Search
  USPC .......... 435/287.1, 288.2, 288.4, 288.7, 304.3, 435/305.1, 305.2, 808
  See application file for complete search history.

(56) References Cited

U.S. PATENT DOCUMENTS

| | | | | |
|---|---|---|---|---|
| 5,096,807 A | * | 3/1992 | Leaback | 435/6 |
| 6,121,042 A | * | 9/2000 | Peterson et al. | 435/284.1 |
| 6,197,575 B1 | | 3/2001 | Griffith et al. | |
| 6,653,124 B1 | | 11/2003 | Freeman | |
| 6,730,471 B1 | * | 5/2004 | Katerkamp et al. | 435/4 |
| 6,943,008 B1 | * | 9/2005 | Ma | 435/297.1 |
| 7,110,107 B2 | | 9/2006 | Martin et al. | |
| 2002/0155594 A1 | * | 10/2002 | Hsieh et al. | 435/299.2 |
| 2002/0173033 A1 | | 11/2002 | Hammerick et al. | |
| 2002/0182241 A1 | | 12/2002 | Borenstein et al. | |
| 2003/0003571 A1 | * | 1/2003 | Kanegasaki et al. | 435/288.5 |
| 2003/0077817 A1 | | 4/2003 | Zarur et al. | |

(Continued)

FOREIGN PATENT DOCUMENTS

WO   2004/101743 A2   11/2004

OTHER PUBLICATIONS

International Search Report & Written Opinion in PCT/US06/60501, mailed on Jul. 18, 2007.

(Continued)

*Primary Examiner* — Nathan Bowers
(74) *Attorney, Agent, or Firm* — Calfee, Halter & Griswold LLP

(57) ABSTRACT

The methods generally relate to three-dimensional culturing of cells with the steps of seeding a cell support structure in a device with at least one vessel for cell culture having a bottom, at least one wall and a cell support structure for three-dimensional cell culture. The cell support structure is inside the at least one vessel and the device is configured such that assays can be performed. Devices for performing cell culture and assays are also provided. It will be understood that the devices can have many different suitable configurations. In general, the devices are selected such that they can be used with suitable radiation based assays.

25 Claims, 24 Drawing Sheets

(56) References Cited

U.S. PATENT DOCUMENTS

| | | | |
|---|---|---|---|
| 2003/0082795 | A1 | 5/2003 | Shuler et al. |
| 2004/0072342 | A1 | 4/2004 | Bothwell et al. |
| 2004/0077075 | A1 | 4/2004 | Jensen et al. |
| 2004/0197367 | A1* | 10/2004 | Rezania et al. ............... 424/422 |
| 2004/0259177 | A1 | 12/2004 | Lowery et al. |
| 2005/0058692 | A1 | 3/2005 | Hai-Quan et al. |
| 2005/0148082 | A1 | 7/2005 | Gilbert et al. |
| 2005/0164376 | A1 | 7/2005 | Balagadde et al. |
| 2005/0239195 | A1* | 10/2005 | Oram et al. ............... 435/288.3 |
| 2005/0260745 | A1 | 11/2005 | Domansky et al. |
| 2006/0019326 | A1 | 1/2006 | Vacanti et al. |
| 2006/0099705 | A1 | 5/2006 | Wikswo et al. |
| 2006/0199260 | A1 | 9/2006 | Zhang et al. |
| 2007/0048731 | A1* | 3/2007 | Colicos et al. ..................... 435/4 |
| 2007/0166816 | A1* | 7/2007 | Campbell et al. .......... 435/288.4 |
| 2007/0178589 | A1* | 8/2007 | Wilson .......................... 435/325 |

OTHER PUBLICATIONS

Kikuchi, H. et al., "Odontoblasts induced from mesenchymal cells of murine dental papillae in three-dimensional cell culture," Cell Tissue Res., vol. 317, pp. 173-185 (Jun. 22, 2004).

Kyle, A. H. et al., "Direct Assessment of Drug Penetration into Tissue Using a Novel Application of Three-Dimensional Cell Culture," Cancer Research, vol. 64, pp. 6304-6309 (Sep. 1, 2004).

Ashcroft et al. "Commercial high speed machines open new opportunities in high throughput flow cytometry (HTFC)." J. Immunol. Methods, Sep. 21, 2000, vol. 243, pp. 13-24.

Borenstein et al. "Microfabrication technology for vascularized tissue engineering." Biomedical Microdevices, 2002, vol. 4, No. 3, pp. 167-175.

Bremer et al. "Establishment of an in vitro reporter gene assay for developmental cardiac toxicity." Toxicology In Vitro, Jun. 2001, vol. 15, No. 3, pp. 215-223.

Daunert et al. "Genetically engineered whole-cell sensing systems: coupling biological recognition with reporter genes." Chemical Reviews, Jun. 21, 2000, vol. 100, No. 7, pp. 2705-2738.

Dimasi et al. "The price of innovation: new estimates of drug development costs." Journal of Health Economics, Mar. 2003, vol. 22, No. 2, pp. 151-185.

Girard et al. "Small-scale bioreactor system for process development and optimization." Biochem. Eng. J., Mar. 2001, vol. 7, No. 2, pp. 117-119.

Gorba et al. "Pharmacological potential of embryonic stem cells." Pharmacol. Res., Apr. 2003, vol. 47, No. 4, pp. 269-278.

Gu et al. "Computerized microfluidic cell culture using elastomeric channels and Braille displays." Proc. Natl. Acad. Sci. USA, Nov. 9, 2004, vol. 101, No. 45, pp. 15861-15866.

Hung et al. "Continuous perfusion microfluidic cell culture array for high-throughput cell-based assays." Biotechnol. Bioeng., Jan. 5, 2005, vol. 89, No. 1, pp. 1-8, (published online Dec. 3, 2004).

Hunt et al. "GFP-expressing mammalian cells for fast, sensitive, noninvasive cell growth assessment in a kinetic mode." Biotechnol. Bioeng., Oct. 20, 1999, vol. 65, No. 2, pp. 201-205.

Hunt et al. "Fluorescent proteins in animal cells for process development: optimization of sodium butyrate treatment as an example." Biotechnol. Bioeng., Mar. 5, 2002, vol. 77, No. 5, pp. 528-537.

Jeon et al. "Neutrophil chemotaxis in linear and complex gradients of interlukin-8 formed in a microfabricated device." Nature Biotechnology, Jul. 2002, vol. 20, pp. 826-830.

Kobayashi et al. "Acquired multicellular-mediated resistance to alkylating agents in cancer." Proc. Natl. Acad. Sci. USA, Apr. 15, 1993, vol. 90, No. 8, pp. 3294-3298.

Leclerc et al. "Microfluidic PDMS (polydimethylsiloxane) bioreactor for large-scale culture of hepatocytes." Biotechnol. Prog., 2004, vol. 20, No. 3, pp. 750-755.

Li et al. "Human cord cell hematopoiesis in three dimensional nonwoven fibrous matrices: in vitro simulation of the marrow microenvironment." Journal of Hematotherapy & Stem Cell Research, Jun. 2001, vol. 10, No. 3, pp. 355-368.

McDonald et al. "Fabrication of microfluidic systems in poly(dimethylsiloxane)." Electrophoresis, Jan. 1, 2000, vol. 21, No. 1, pp. 27-40.

Mueller-Klieser, W. "Three-dimensional cell cultures: from molecular mechanisms to clinical applications." Am J Physiol Cell Physiol, Oct. 1997, vol. 273, No. 4, pp. C1109-C1123.

Ostrovidov et al. "Membrane-based PDMS microbioreactor for perfused 3D primary rat hepatocyte cultures." Biomedical Microdevices, 2004, vol. 6, No. 4, pp. 279-287.

Paparella et al. "The use of quantitative image analysis in the assessment of in vitro embryotoxicity endpoints based on a novel embryonic stem cell clone with endoderm-related GFP expression." Toxicology In Vitro, Oct. 2002, vol. 16, No. 5, pp. 589-597.

Park et al. "Integration of cell culture and microfabrication technology." Biotechnol. Prog., 2003, vol. 19, No. 2, pp. 243-253.

Peterson et al. "Poly(dimethylsiloxane) thin films as biocompatible coatings for microfluidic devices: Cell culture and flow studies with glial cells." Journal of Biomedical Materials Research Part A, Jan. 1, 2005, vol. 72A, No. 1, pp. 10-18.

Powers et al. "Functional behavior of primary rat liver cells in a three-dimensional perfused microarray bioreactor." Tissue Engineering, Jul. 2002, vol. 8, No. 3, pp. 499-513.

Ramirez et al. "High-throughput flow cytometry: validation in microvolume bioassays." Cytometry Part A, May 2003, vol. 53A, No. 1, pp. 55-65.

Ries et al. "The annual report to the nation on the status of cancer, 1973-1997, with a special section on colorectal cancer." Cancer, May 15, 2000, vol. 88, No. 10, pp. 2398-2424.

Scholz et al. "Prevalidation of the embryonic stem cell test (EST)—a new in vitro embryotoxicity test." Toxicology In Vitro, Aug.-Oct. 1999, vol. 13, Nos. 4-5, pp. 675-681.

Sia et al. "Microfluidic devices fabricated in poly(dimethylsiloxane) for biological studies." Electrophoresis, Nov. 2003, vol. 24, No. 21, pp. 3563-3576.

Sin et al. "The design and fabrication of three-chambered microscale cell culture analog devices with integrated dissolved oxygen sensors." Biotechnol. Prog., 2004, vol. 20, No. 1, pp. 338-345 (published online Nov. 5, 2003).

Smitskamp-Wilms et al. "Postconfluent multilayered cell line cultures for selective screening of gemcitabine." Eur. J. Cancer, May 1998, vol. 34, No. 6, pp. 921-926.

Snyder et al. "Microscale three-dimensional polymeric platforms for in vitro cell culture systems." J. Biomater. Sci. Polymer Edn., Sep. 1, 2001, vol. 12, No. 8, pp. 921-931.

Szita et al. "Development of a multiplexed microbioreactor system for high-throughput bioprocessing." Lab Chip, 2005, vol. 5, pp. 819-826 (published online Jun. 30, 2005).

Thompson et al. "Dynamic gene expression profiling using a microfabricated living cell assay." Anal. Chem., Jun. 9, 2004, vol. 76, No. 14, pp. 4098-4103.

Verkman A. S. "Drug discovery in academia." Am J Physiol Cell Physiol, Mar. 2004, vol. 286, No. 3, pp. C465-C474.

Viravaidya et al. "Development of a microscale cell culture analog to probe naphthalene toxicity." Biotechnol. Prog., 2004, vol. 20, No. 1, pp. 316-323 (published online Sep. 26, 2003).

Viravaidya et al. "Incorporation of 3T3-L1 cells to mimic bioaccumulation in a microscale cell culture analog device for toxicity studies." Biotechnol. Prog., 2004, vol. 20, No. 2, pp. 590-597 (published online Dec. 12, 2003).

Whitesides et al. "Soft lithography in biology and biochemistry." Annu. Rev. Biomed. Eng., Aug. 2001, vol. 3, pp. 335-373.

Yamada et al. "Mechanisms of fibronectin and integrin function during cell adhesion and migration." Cold Spring Harbor Symposia on Quantitative Biology, 1992, vol. 57, pp. 203-212.

Yang et al. "A fibrous-bed bioreactor for continuous production of monoclonal antibody by hybridoma." Adv. Biochem. Eng. Biotechnol., 2004, vol. 87, pp. 61-96.

Zanzotto et al. "Membrane-aerated microbioreactor for high-throughput bioprocessing." Biotechnol. Bioeng., Jul. 20, 2004, vol. 87, No. 2, pp. 243-254.

* cited by examiner

A.

B.

C.

A

B

C

A

B

C

MATERIALS AND METHODS FOR CELL-BASED ASSAYS

CROSS REFERENCE TO RELATED APPLICATIONS

This application claims priority to and any other benefit of U.S. Provisional Application Ser. No. 60/732,820, filed on Nov. 2, 2005, and U.S. Provisional Application Ser. No. 60/732,821, filed on Nov. 2, 2005, the entire contents of which are incorporated by reference herein.

BACKGROUND

In vitro experiments, especially cell culture systems, have been extensively used for cytotoxicity studies. However, there are several major problems associated with conventional in vitro cytotoxicity assays that use static multi-well plate cultures. According to some such conventional methods, cells are cultured on two-dimensional surfaces, which may camouflage authentic cellular responses that would occur in vivo, where cells exhibit morphology and interact with each other in a three-dimensional milieu. According to other conventional methods, cells are cultured in suspension. A relatively long-term response to antigens or foreign materials (e.g., chemicals and manufactured nanomaterials) can rarely be measured due to metabolic-waste accumulation in the culture. Another disadvantage to both systems is that growth inhibition of the cultured cells is usually judged at an arbitrary point of time, lacking a dynamic long-term monitoring.

Cell culture methods that utilize 2-D cultures for cytotoxicity analyses are inherently prone to error because of the lack of a 3-D scaffold to support cell growth and proper tissue function. Reported research depicts the variation of cellular performance seen between 2-D and 3-D cell cultures including morphological, growth kinetics, growth factor expression, and other functional properties. It is evident that the 3-D culture conditions are important for in vivo-like differentiation, proliferation, metastatic potential of the tumor cells, and development of characteristic heterogeneity within the tumor population.

To mimic the native tissue for in vitro toxicity study models, the key concept is that there is a strong relationship between tissue structure and function. Therefore, in order to achieve the desired functional attributes in a tissue-engineered construct, the culture environment must represent the native counterpart. An important component in a tissue-engineered construct that allows for in vivo-like culture is a 3-D scaffold that allows cell population support, organization, and function.

So far, almost all cell based assays have been developed in 2-D culture systems, although conventional 2-D cultures usually suffer from contact inhibition and a loss of native cell morphology and functionality. In drug discovery, probably the least developed field is to reform in vivo tissue behaviors in in vitro assays, especially the development of in vitro models with cells in their unactivated or quiescent status. Currently, pharmaceutical firms spend large amounts of money on compound efficacy and cytotoxicity tests. However, there is still a 78% failure rate for all drugs, which may be devastating to developing companies. Effective compounds in vitro may be non-effective in vivo for many reasons, including differences between in vitro and in vivo target biology, interrelated biochemical mechanism, metabolism, poor penetration into solid tissues, etc. In comparison with 2-D cultures, 3-D cell models create a more realistic representation of real human tissues, which is critical to many important cell functions, including morphogenesis, cell metabolism, gene expression, differentiation and cell-cell interactions. Discrepancies in predicted drug treatment effectiveness in 2-D and 3-D cultures implicate the advantage of using 3-D culture systems. For cell-based sensing, particularly in studying cytotoxicity and drug discovery, maintaining cells in their native functional state in a proper 3-D environment would improve predictions and have the potential to reduce clinical trial failures.

SUMMARY OF THE INVENTION

According to various embodiments, provided herein are methods and apparatuses for analyzing cellular function of cells in three-dimensional culture. The methods and apparatuses provide for culturing cells by seeding for culture a cell of interest within a cell support structure that includes at least one scaffold that is of a suitable porosity to permit the transmission of at least one form of radiant energy therethrough. The cell support structure is adapted to facilitate three-dimensional cell growth therein. According to the various embodiments further described herein, the cell support structure is anchored within a vessel that is adapted to contain a fluid and is formed of a material suitable for use in at least one of radiation emitting, light transmission, fluorometric, and calorimetric assays.

In various embodiments of the methods hereof, the seeded cell is cultured in a suitable fluid disposed within the vessel so as to promote proliferation of the cell. At one or more appropriate intervals, the culture is treated with one or more test conditions such that a change in the culture is detectable using at least one of radiation emitting, light transmission, fluorometric, and calorimetric assays. Subsequent to treatment, the treated culture may be subjected to analysis by one or more methods involving the transmission of one or more forms of radiant energy so as to detect a change in the culture.

It is to be understood that both the foregoing general description and the following detailed description are exemplary and explanatory only and are not restrictive of the materials and methods, as claimed.

BRIEF DESCRIPTION OF THE DRAWINGS

The following detailed description of embodiments of the present materials and methods can be best understood when read in conjunction with the following drawings, where like structure is indicated with like reference numerals and in which.

DESCRIPTION OF THE EMBODIMENTS

Figure 1:
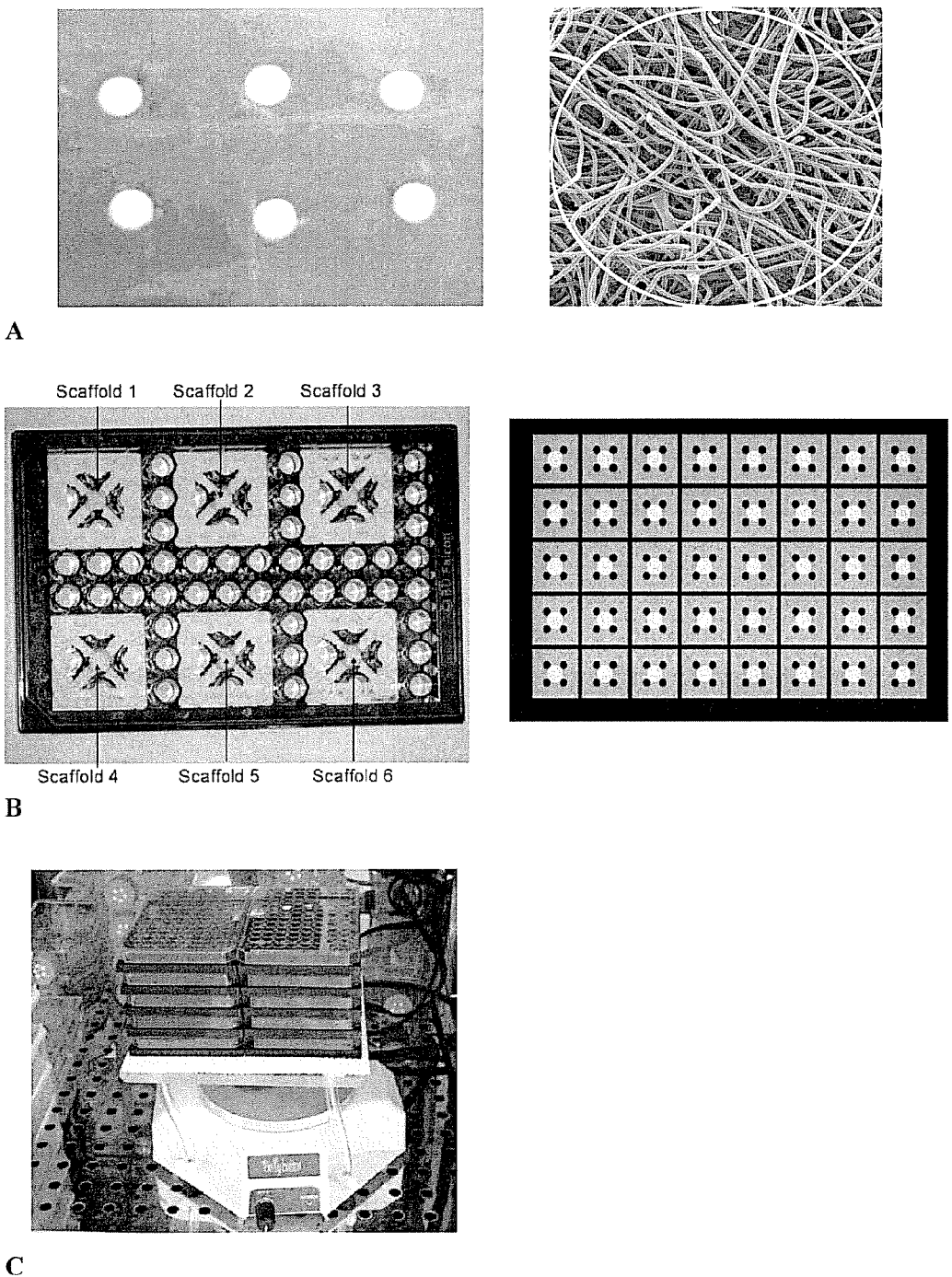
FIG. 1 illustrates three-dimensional cell cultures in a microbioreactor array fabricated by modifying multiwell plates. A. Fibrous matrices cut into a disk-shape before being put into the microbioreactors on a multiwell plate. B. Multiwell microbioreactors each with one fibrous disk as the scaffold for cells fixed at the center. Each microbioreactor is a square chamber consisting of a center well and eight surrounding wells with their original walls removed to allow medium exchange between the cells grown in the center well and the medium in the surroundings. There are 6 microbioreactors on a 96-well plate (left) and 40 microbioreactors on a 384-well plate (right). C. Multiwell plates, after seeding cells into the fibrous matrices in the microbioreactors, are stacked on a shaker in an incubator.

The present materials and methods will now be described by reference to more detailed embodiments, with occasional reference to the accompanying drawings. These materials and methods may, however, be embodied in different forms and should not be construed as limited to the embodiments set forth herein. Rather, these embodiments are provided so that this disclosure will be thorough and complete, and will fully convey the scope of the materials and methods to those skilled in the art.

Unless otherwise defined, all technical and scientific terms used herein have the same meaning as commonly understood by one of ordinary skill in the art to which these materials and methods belong. The terminology used in the description of the embodiments herein is for describing particular embodiments only and is not intended to be limiting of the materials and methods. As used in the description of the embodiments and the appended claims, the singular forms "a," "an," and "the" are intended to include the plural forms as well, unless the context clearly indicates otherwise. All publications, patent applications, patents, and other references mentioned herein are incorporated by reference in their entirety.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present materials and methods. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the materials and methods are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

The methods generally relate to three-dimensional culturing of cells with the steps of seeding a cell support structure in a device with at least one vessel for cell culture having a bottom, at least one wall and a cell support structure for three-dimensional cell culture. The cell support structure is inside the at least one vessel and the device is configured such that assays can be performed. Three-dimensional cell culture is an in vitro model for mimicking native tissue growth. The cell support culture structure allows for in vivo like culture via a three-dimensional scaffold that allows cell population support, organization and function. The three-dimensional scaffold provides a representative in vitro tissue culture model for native in vivo tissue by utilizing a three-dimensional matrix to stimulate the in vivo structural environment. Furthermore, the methods provide a media in a quantity to allow cell proliferation. The media may be chosen from any suitable media for the type of cell being cultured. For example, Dulbecco's Modified Eagle Media (DMEM) is a common choice for mammalian cell culture. In static three-dimensional culture a quantity of media is necessary to allow dilution of background noise and waste products from non-viable cells. In dynamic flow three-dimensional culture a flow rate to perfuse the cell support structure and remove background noise and waste products from non-viable cells can be determined. Agitation for the static three-dimensional culture can be provided by placing the device on a shaker set to an appropriate speed to sufficiently mix the media. Agitation for the dynamic flow three-dimensional culture can be provided by the flow of media through the vessel.

The cells that can be cultured in the device can be chosen from any suitable cell for three-dimensional culturing. Examples of such cells include mammalian cells, embryonic stem cells, cancer cells, colon cancer cells, Chinese hamster ovary cells, NIH 3T3 cells, human embryonic cells and microorganisms. The cells can provide a non-invasive means for measuring cell growth and/or responses to environmental stimuli. Such means, for example, are expression of light emitting proteins, radioactivity, or biochemical markers. The cells can be transfected and/or selected for stable expression of a light-emitting protein by standard procedures known in the art. The cells can express any light-emitting protein, such as firefly luciferase, Aequorin, GFP from jellyfish *Aequorea victoria* and its variants (BFP, CFP, EGFP, YFP, dEGFP), and DsRed Fluorescent Protein from *Discosoma* sp. reef coral, and enzymes that can produce fluorescent or color products or consume fluorescent or color substrates, or poly-esterified derivatives of fluorescein such as Calcein AM.

The device is contemplated to be used for cellular assays. Such assays include cytotoxicity assays for drug screening and/or discovery. Other assays include biosensor assays, where the cells can be used to detect molecules present in the environment, media and process optimization assays, and embryonic stem cell proliferation and/or differentiation assays.

Fluorescence quantification of the cells cultured in and/or on the cell support structure is also contemplated. Quantitation of the fluorescence can allow one of ordinary skill in the art to monitor cell proliferation. Cell proliferation can be a useful marker to indicate toxicity of a test compound in the media perfusing the cell support structure. If a test compound is toxic cell proliferation would either slow or cease. If cell proliferation slowed or ceased the expression of a detectable biomarker would correspondingly slow or cease and can be detected by suitable optical methods, including fluorescence, radiation and/or light emission. Fluorescence sensors can also be used to detect changes in the pH and/or dissolved oxygen of the media perfusing the cell support structure and cultured cells.

In accordance with embodiments of the present invention, devices for performing cell culture and assays are provided. It will be understood that the devices can have many different suitable configurations. In general, the devices are selected such that they can be used with suitable radiation based assays.

Figure 22:
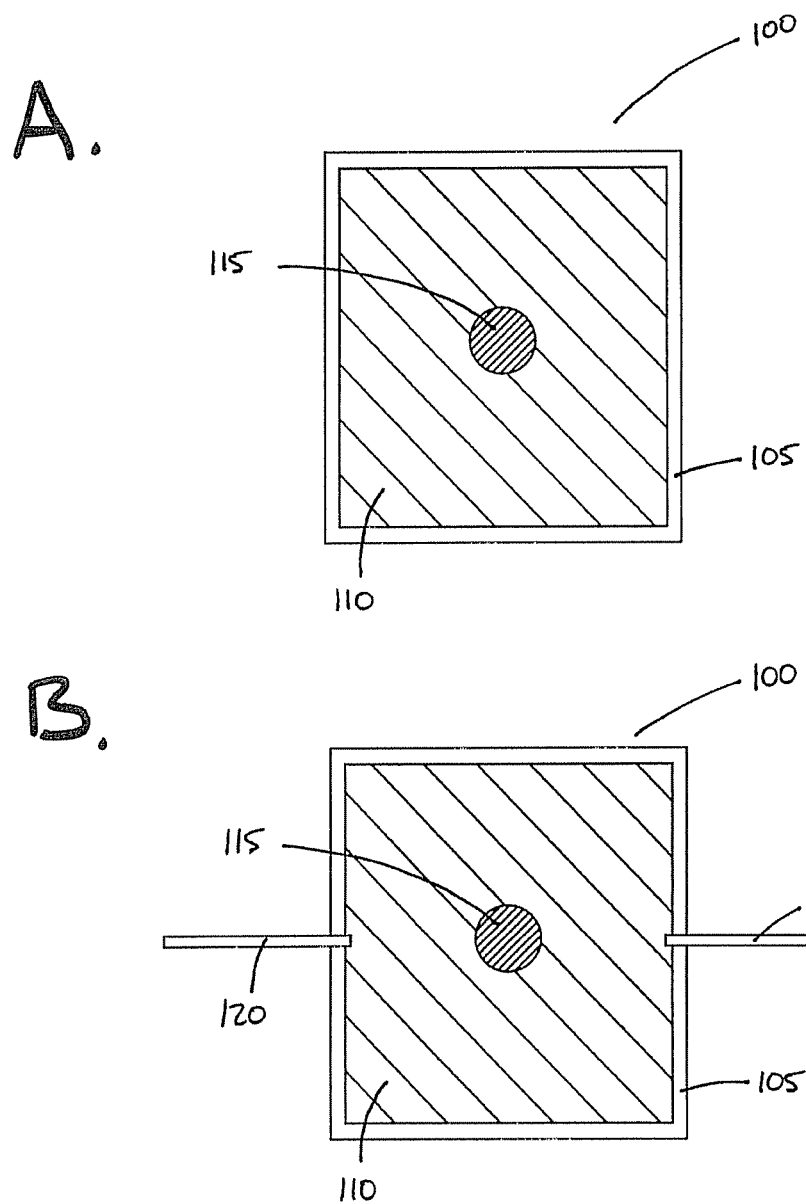
FIG. 22 illustrates a schematic view of A. device 100 with walls 105, a bottom 110 and a cell support structure 115; B. the device 100 with walls 105, a bottom 110, a cell support structure 115 and ports 120 and 125.

Referring now to FIG. 22A, a device 100 is illustrated. The device 100 comprises a vessel 110 having at least one wall 105. The vessel 110 may be of any suitable shape and have any suitable number of walls. For example, the vessel 110 may be of a circular, square, oval, rectangular, or irregular shape. The vessel 110 may be made from any suitable material. For example, the material may be selected such that radiation of interest used in a particular assay will pass though the vessel without undue interference or scattering. The vessel 110 may be of any suitable dimensions. In some examples, the vessel 110 has dimensions chosen such that the surface area of the vessel minus the surface area covered by the cell support structure 115 is greater than the surface area of the cell support structure 115. This will be discussed further herein. The vessel 110 may be provided with a lid or other covering (not shown).

The vessel 110 further has at least one cell support structure 115 provided inside the vessel 110. The cell support structure 115 may be provided in any suitable location inside the vessel 110. For example, the cell support structure 115 may be provided proximate to the bottom of the vessel 110 or proximate to a wall 105 of the vessel. The cell support structure 115 is provided in the vessel 110 such that a fluid may be used to cover the cell support structure 115 such that cells may be cultured in the cell support structure 115. In some examples, the cell support structure 115 may be secured to the bottom or wall 105 of the vessel 110 to ensure that the cell support structure 115 does not float. The cell support structure 115 may be secured in any suitable manner. For example, the cell support structure 115 may be adhered to vessel 110 using a suitable adhesive. In another example, the cell support structure 115 may be mechanically attached to the vessel 110 using any suitable mechanical attachment or restraint, examples of which include, but are not limited to screws, nails, hooks, loops, and snaps, and combinations thereof. In yet a further example, the cell support structure 115 may be secured to a portion of the vessel 110 that contains structures (not shown) that compress around the cell support structure 115.

The cell support structure 115 may be chosen to have any suitable shape and be made from any suitable material. The cell support structure 115 is chosen such that three-dimensional cell cultures may be grown using the cell support structure 115. Additionally, the cell support structure 115 is generally chosen so as not to provide undue interference with the assay. In some examples, the cell support structure is a fibrous material, a porous material, or both. For example, natural or synthetic fibers may be used as the cell support structure. The cell support structure may be treated or untreated. The fibers may be woven or non-woven. In one example, the cell support structure 115 may be non-woven polyethylene terephthalate, polyethylene, polypropylene, polycarbonate, polystyrene, polyesters, polyurethanes, polyanhydrides, Nylon, cotton, polylactic acid (PLA), polyglycolic acid (PGA), PLGA, polycaprolactone (PCL), polymer of hyaluronic acid benzyl ester, carbon fiber, and collagen fiber. The materials also can be either gel or foam made of alginate, chitosan, fibrin, hydroxyapatite, ceramics, or gelatin or agarose hydrogel.

In some examples, needle-punched polyethylene terephthalate PET fabric (fiber diameter, ~20 μm; fiber density, 1.35 g/cm$^3$) may be used as the cell support structures. Cake-shaped cell support structures may be cut with any suitable dimensions. For example, the cell support structures may have 0.1 cm height and 0.3 cm$^2$ bottom surface area, the same dimension as the wells of 96-well plates (FIG. 1A).

The PET may be treated. For example, PET matrices may be treated before use to increase the cell attachment efficiency. Solution with 1% (v/v) Na$_2$CO$_3$ and 1% (v/v) Tween-20 was heated to 60° C. and PET matrices may be soaked in the above solution for 30-60 min at 60° C. After being rinsed with distilled water several times, PET matrices can be transferred to 1% (v/v) NaOH solution and boiled for 30-60 min. After being thoroughly washed with distilled water again, scaffolds giving similar fluorescent backgrounds may be selected by a Cytofluor Series 4000 at gain 50 (excitation at 485 nm with a bandwidth of 20 nm and emission at 530 nm with a bandwidth of 25 nm), which may be the same equipment and measurement conditions used for all later live cell fluorescent quantification. Scaffolds may then be soaked in PBS, sterilized in an autoclave at 121° C. for 20 min and stored in room temperature for future uses. Scaffolds may then be soaked in growth medium for 12 h before use. Before inoculation with cells, the growth medium may be removed from the scaffolds.

Figure 23:
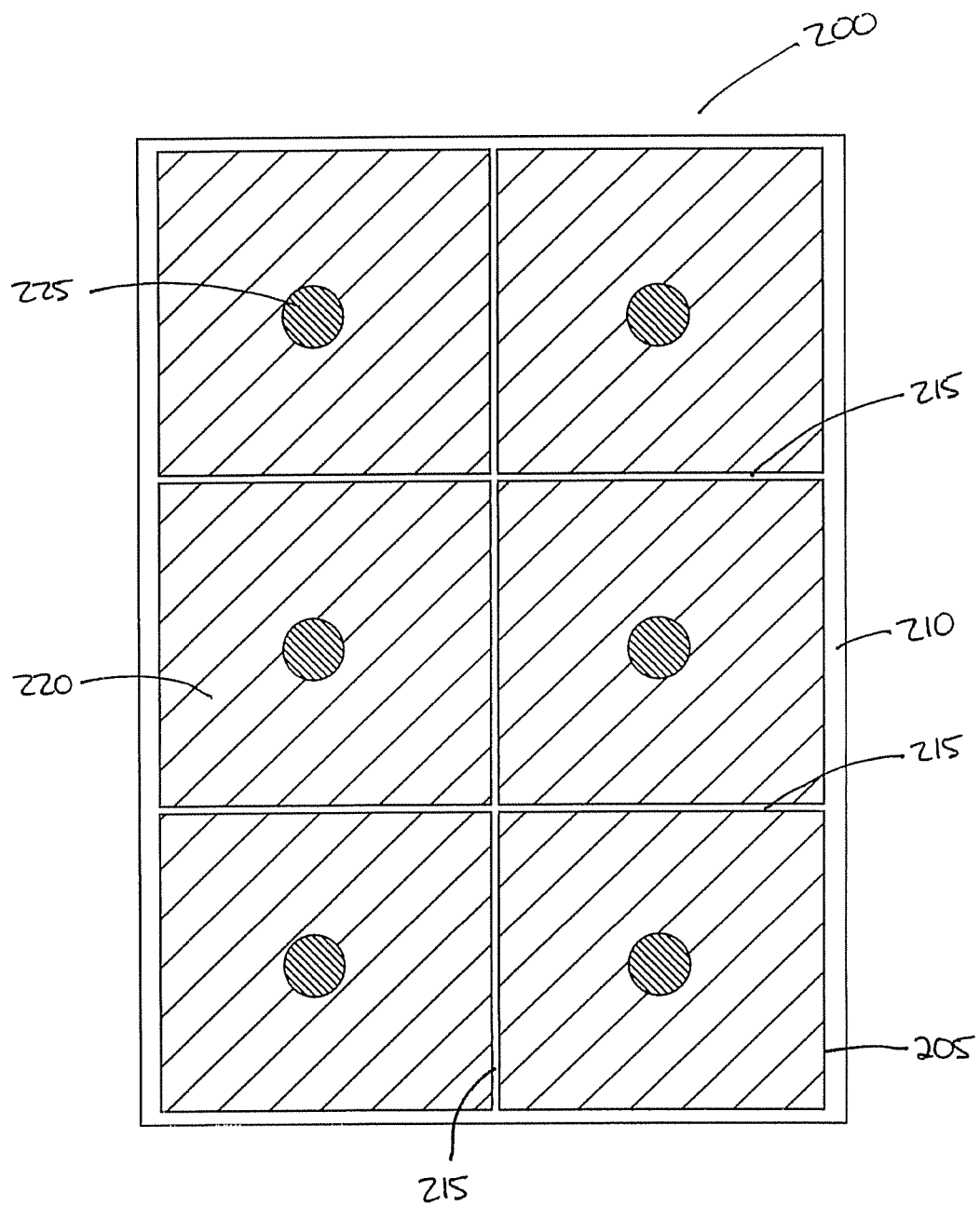
FIG. 23 illustrates a schematic view of device 200 with six vessels 205, with walls 210, dividers 215, a bottom 220 and a cell support structure 225 in each of the six vessels 205.
Figure 24:
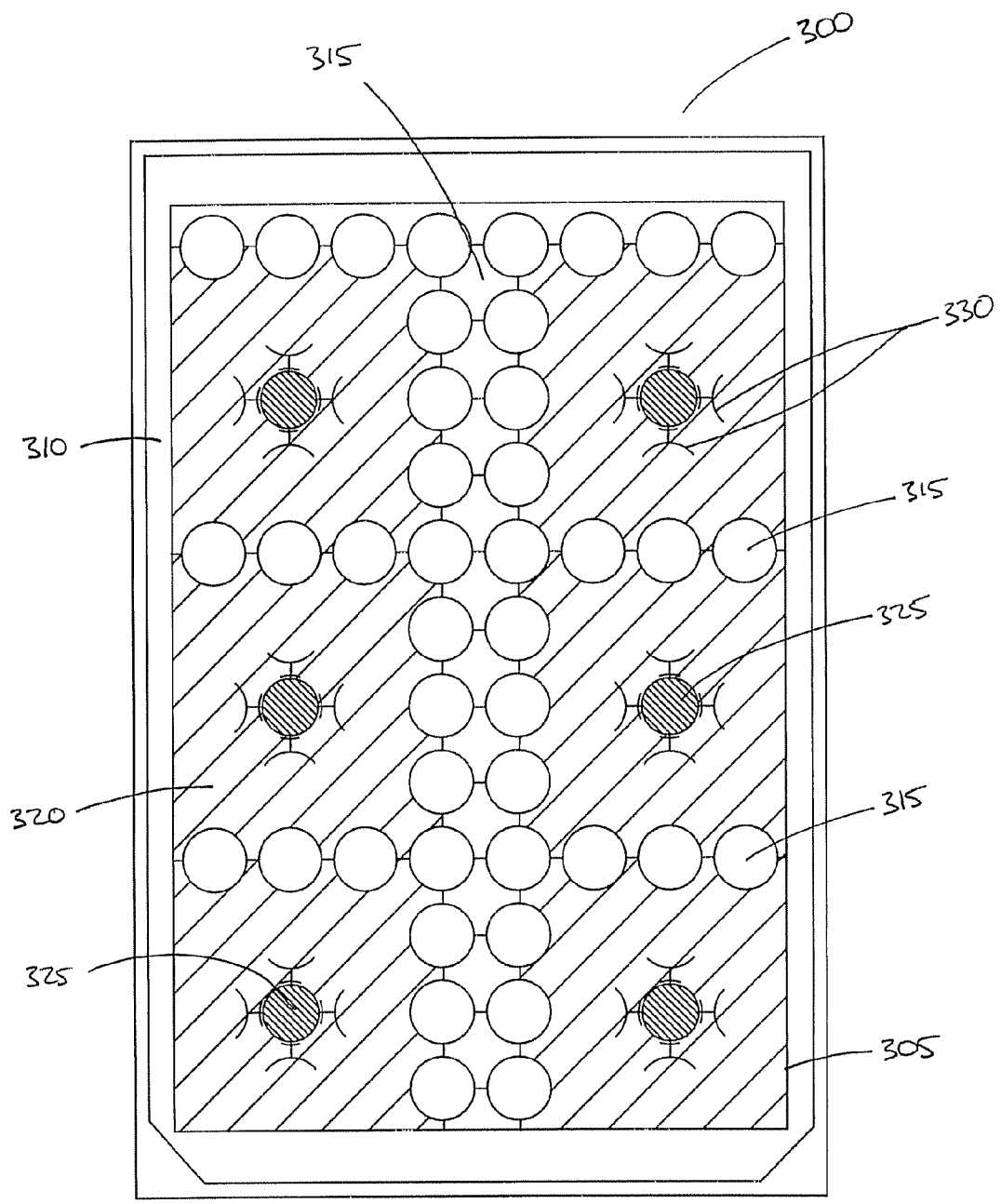
FIG. 24 illustrates a schematic view of device 300 with six vessels 305, walls 310, dividers 315, a bottom 320, a cell support structure 325 in each of the six vessels 305 and cell support structure holders 330.

In some embodiments, multiple vessels 110 may be provided on a single plate. Such embodiments are illustrated in FIGS. 23 and 24. In FIG. 23, a device 200 having six vessels 205 with walls 210, dividers 215, a bottom 220, and at least one cell support structure 225 in each vessel 205 is shown. Such a device having a multiple member of vessels may be useful for allowing assays to be performed on more than three-dimensional cell culture at one time. FIG. 24 illustrates an alternative embodiment. A device 300 having six vessels 205, with walls 210, dividers 215, and a bottom 220 are shown. The device 300 also has cell support structure holders 330 that compress and hold the cell support structure 325 in each vessel 305. It will be understood that the materials, sizes, and cell support structures may be chosen to be of any suitable type and dimension as discussed above.

For example, FIG. 1 illustrates three-dimensional cell cultures in devices fabricated by modifying commercially available multi-well plates. In this platform, cell support structures were cut into a disk-shape (FIG. 1A) before putting into vessels on the multi-well plate (FIG. 1B). Each vessel on the plate contains one cell support structure, as the scaffold for cells, fixed in the vessels, which consist of a center well and eight surrounding wells with their original walls removed to allow medium exchange between the cells grown in the center well and the medium in the surroundings. There are 6 vessels on a 96-well plate (FIG. 1B, left) and 40 vessels on a 384-well plate (FIG. 1B, right). The plates, after seeding cells into the cell support structures in the vessels, may be stacked on a shaker and incubated in an incubator (FIG. 1C).

Figure 2:
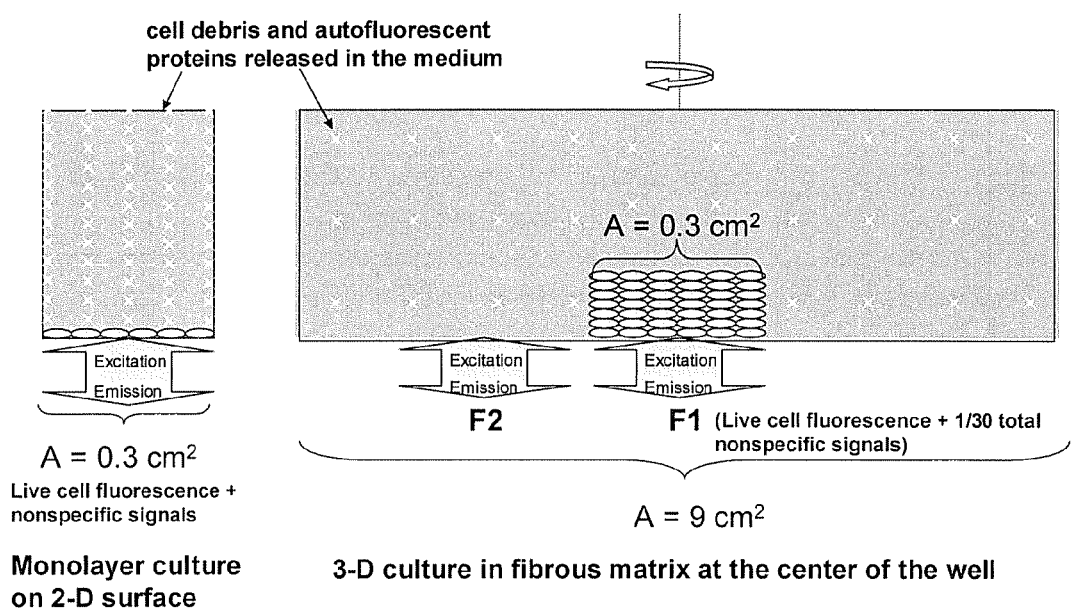
FIG. 2 illustrates that 3-D cell culture in a microbioreactor on a multiwell plate can give higher light intensity with lower background noise that can be subsequently subtracted after online measurements.

As shown in FIG. 2, the total bottom area in each vessel is larger than the area where light will be emitted from the cells present in the cell support structure. This allows for intensified light signal emitting from the live cells while diluting any interference or background noise generated from medium components, cell debris, and light-emitting proteins released from dead cells. The area without the cell support structure provides online background measurements for noise deduction. It also gives sufficient volume to contain additional medium for diluting toxic metabolites such as lactic acid and ammonia produced by the cells and providing plenty of nutrients for sustainable long-term culture without the necessity of frequent fluid change. In this examples, the device fabricated on the 96-well plate has a center well area of ~0.3 cm$^2$, ~9 cm$^2$ of total chamber surface area, and can hold about 4 ml of liquid fluid. For devices fabricated on the 384-well plate, each has a center well area of ~0.125 cm$^2$, 1.5 cm$^2$ of total chamber surface area, and can hold about 0.8 ml of liquid media.

Referring now to FIG. 22B, another embodiment of a device 100 is shown. The device 100 has a vessel 110 with at least one wall 105 and at least one cell support structure 110 as discussed above. The device 100 additionally has first and second ports 120, 125. The first and second ports 120, 125 are in fluid communication with the interior of the vessel 110. The first and second ports 120, 125 are disposed such that fluid can flow from the first port 120 to the second port 125. It will be understood that any suitable additional number of ports could be provided. The ports 120, 125 may be used to introduce new fluid or any other components to a cell culture in the vessel 110. In one example, a pump could be provided that would be used to automatically perfuse fluid via the first port 120, the second port 125 or a combination thereof.

Figure 25:
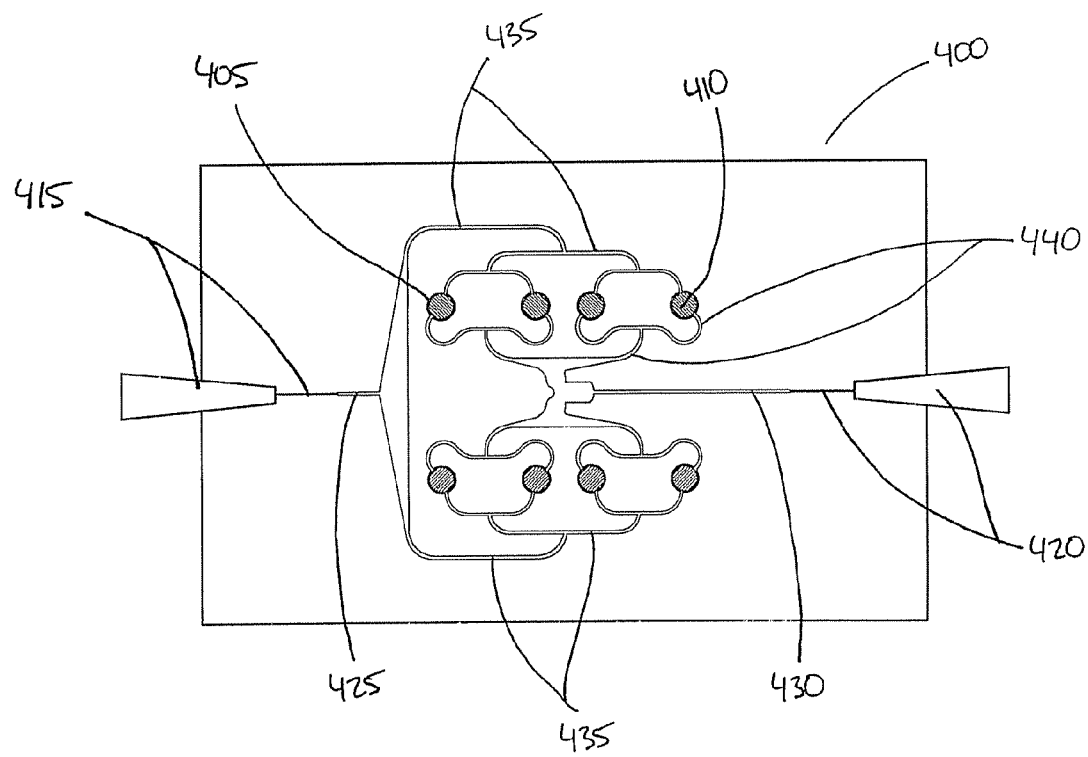
FIG. 25 illustrates a schematic view of device 400 with eight vessels 405 containing cell support structure 410, first port 415, second port 420, first channel 425, second channel 430, first branch channels 435 and second branch channels 440.

Referring now to FIG. 25, another embodiment of a device 400 is illustrated. The device 400 provides channels that allow a fluid to be perfused through the device 400. The device has a plurality of vessels 405 and each vessel 405 has a cell support structure 410 provided in the vessel 405. First and second ports 415 and 420 are provided. The first and second ports 415, 420 are disposed such that a fluid can flow from the first port 415 to the second port 420. The first and second ports 415, 420 are in communication via channels that are provided through the device 400. A first channel 425 flows to first branch channels 435. The branch channels 435 branch from the first channel and flow to the plurality of vessels 405. Second branch channels 440 carry fluid out of the plurality of vessels and to the second channel 430. The second channel 430 is in communication with the second port 420, and fluid flows from the second channel 430 out the second port. In this manner, fluid may be provided in a continuous or non-continuous flow through the device 400. The perfusion allows continuous removal of metabolic waste and supply of nutrients at a physiological rate. The continuous flow may be driven be syringe pumping or in any other suitable manner. The waste may be gathered from ports, such as the second port 420, for further analysis.

It will be understood that any suitable number of vessels 405 could be provided in any suitable configuration. It will be further understood that more than two ports could be provided. For example, three, four, five, six, seven, eight, etc. ports could be provided. Each port could be in communication with some or all of the channels provided in a particular device depending on how the channels and vessels are configured. It may be desirable to have separate series of vessels served by separate sets of ports on the same device so that a higher throughput assay could be performed. It will be further understood that the vessels 405 may be interconnected such that fluid flows from one vessel into as subsequent vessel. In other examples, the vessels 405 may be served by channels such that fluid does not flow from one vessel into a subsequent vessel as shown in FIG. 25. The device 400 may be operated as a continuous reactor to form three dimensional cell cultures in each vessel 405.

The device 400 may be made in any suitable manner and have any suitable dimensions. The devices 400 are generally sized such that they may be used in conjunction with a suitable assay. In some instances, it may be desirable for the channels to have dimensions on the micro scale such that small amounts of fluid can be used for continuous operation. In other examples, porous biocompatible materials, such as fibrous polymers may be used to fill some or all of the channels to provide additional control of flow patterns.

The device 400 may be made from any suitable material. For example, polymeric materials may be used. Such polymeric materials include, but are not limited to, polydimethylsiloxane (PDMS), polymethylmethacrylate (PMMA), polystyrene, polyesters, and poly(glycerol-sebacate) or PGS. The device 400 may be formed in any suitable manner. For example, when a polymer is used, features of the device 400 may be photolithographically defined on a substrate, and the substrate may be used as a mold into which the uncured polymer is provided. The polymer may be subsequently cured to form the device 400 having the features. In this instance a lid may be provided to form the top of the device 400.

A non-interference network for an array of cell culture wells to prevent unwanted convective and diffusive mixing is also included, which may be applied to other high-throughput microfluidic arrays, such as for molecular assays. Fluorescence sensors for pH and dissolved oxygen may also be easily included in microscale chambers connected to cell culture wells.

Figure 26:
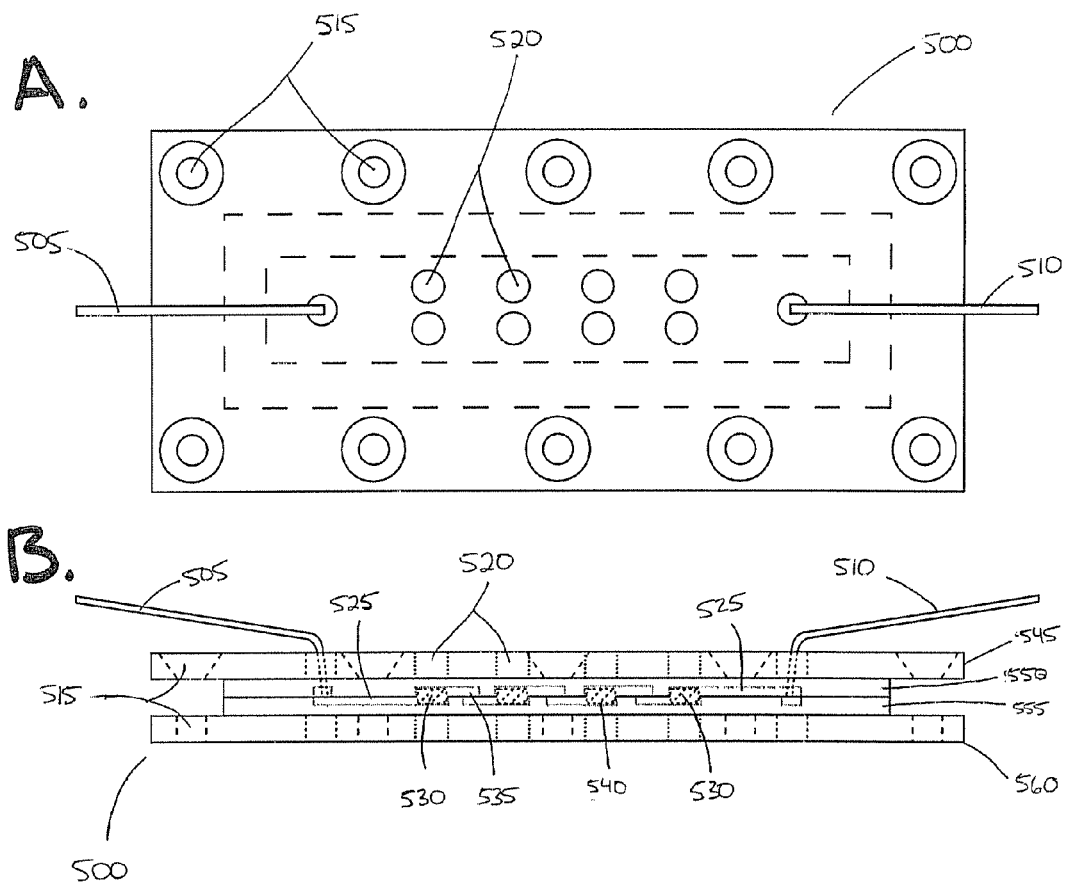
FIG. 26 illustrates a schematic view of device 500 A. from the top, and B. from the side.
Figure 27:
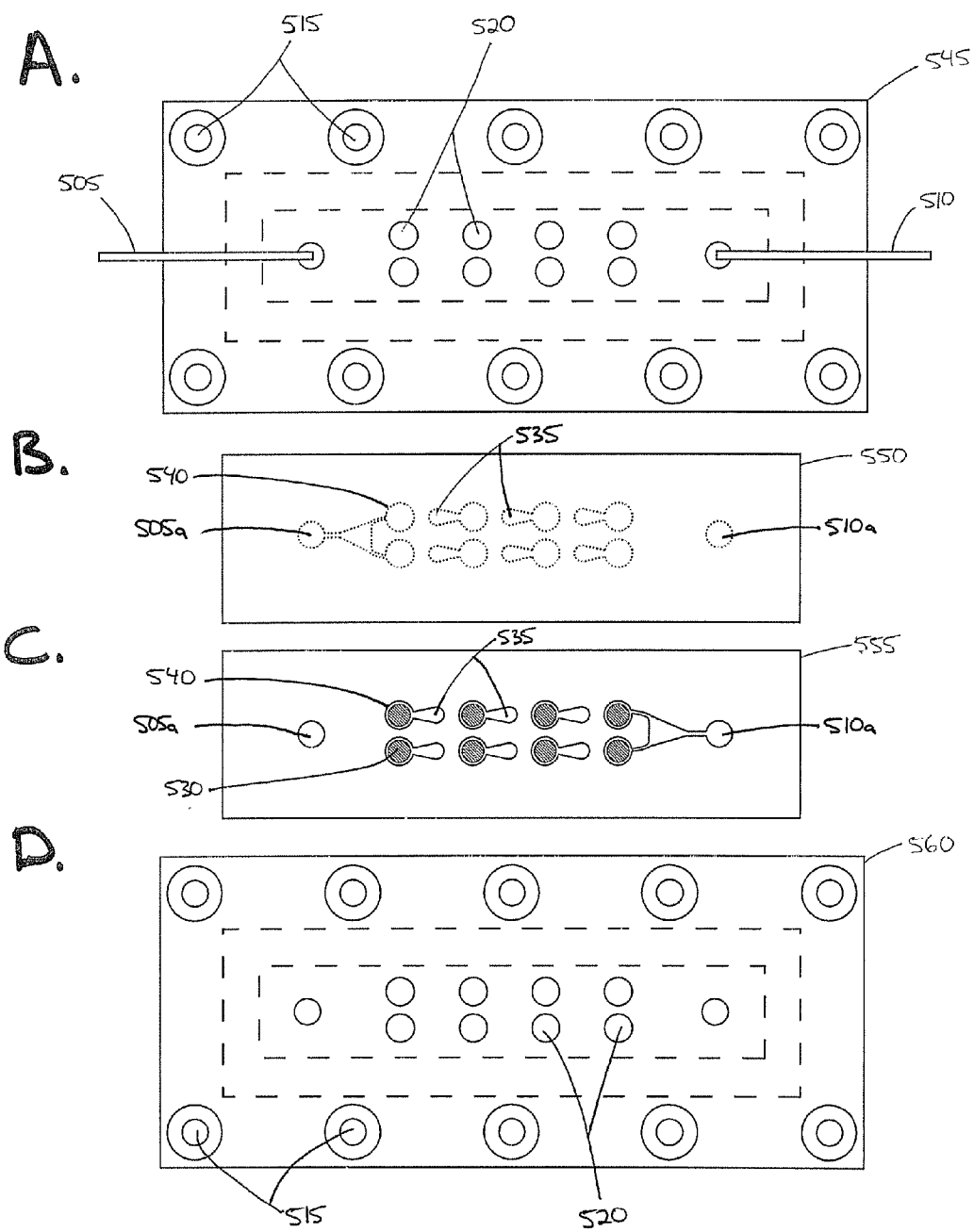
FIG. 27 illustrates an explodes schematic view of device 500 A. top view of substrate 545; B. top view of substrate 550; C. top view of substrate 555; and D. top view of substrate 560.

Referring now to FIGS. 26 and 27, another embodiment of a device 500 having channels 535 is provided. The device 500 has a top 545, first layer 550, second layer 555 and bottom 560. The top 545 and bottom 560 may be any suitable material that may be used to compress the first layer 550 and the second layer 555. The first layer 550 has vessels 540 and relay channels 535 formed therein. Additionally, the first layer has a first port area 505*a* and a second port area 510*a* where fluid flow into and out of the first layer. The second layer also has vessels 540, relay channels 535, and first and second port areas 505*a*, 510*a*. Additionally, the second layer has cell support structures 530 provided in the vessels 540. The first layer 550 and the second layer 555 are placed proximate to one another as shown in FIG. 26B. The first layer 550 and the second layer 555 thus form a plurality of vessels 540 having relay channels 535 connecting at least some of the vessels 540 in series. The relay channels are formed such that fluid flows into the device via the first port area 505*a*, along a channel to a first vessel 540, out of the top of the vessel 540 via the relay channel 535, down to the adjacent relay channel 535, and into the next vessel 540 in the series from the bottom. In this manner, filling of the vessels 540 from the bottom may be achieved. The top layer 545 has holes 520 that correspond to the vessels 540. Additionally, attachment points 515 and first and second ports 505, 510 are provided. The bottom layer 560 also has holes 520 that correspond to the vessels 540 and attachment points 515. The first and second layers 550, 555 may be sandwiched between the top 545 and bottom 560. The top and bottom 545, 560 may then be attached at the attachment points 515 in any suitable manner to provide support for the device 500.

It will be understood that the layers may be made from any suitable materials. For example, the first and second layers 550, 555 may be formed in accordance with the embodiment illustrated in FIG. 25. The top and bottom 545, 560 may be formed from any suitable support structure. For example, plastic or metal could be used. It will be further understood that the device 500 could be formed from multiple first and second layers 550, 555. For example, four or more layers could be provided having larger volume vessels 540 or having a larger number of vessels 540 because each set of two layers have vessels 540 provided therein.

It will be understood that the device 500 may have any suitable dimensions. In addition, the device 500 could have any suitable number of vessels arranged in any suitable manner. For example, the vessels 540 could be arranged in series or in series and parallel as shown in the figures.

EXAMPLES

Example 1

Effects of Serum and Fibronectin on Cell Cultures

Figure 7:
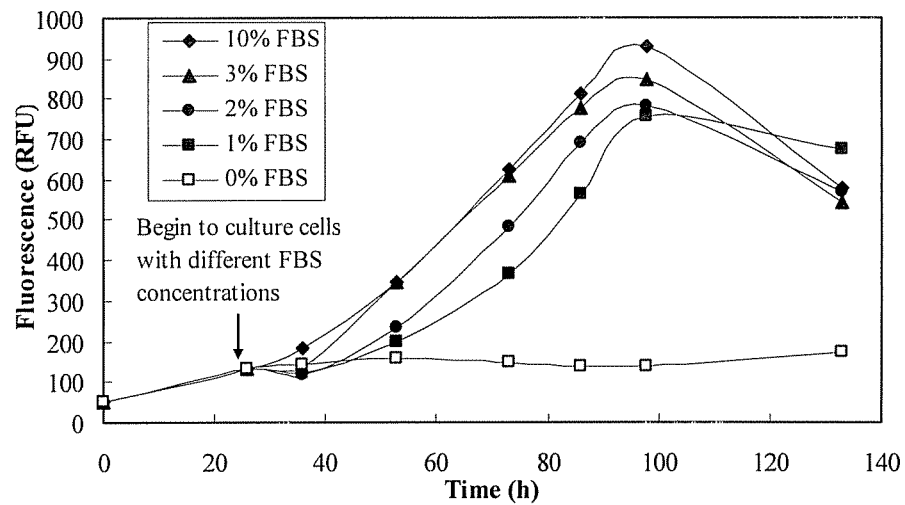
FIG. 7 illustrates ES-GFP cultures used to investigate the effects of FBS on cell growth.

Embryonic stem (ES) cells transfected with constitutive CMV promoter, which is cell cycle sensitive, and a gene encoding a light-emitting protein (e.g., EGFP) can be used for studying proliferation and dynamic responses to growth factor or stimuli. Fetal bovine serum (FBS) is an essential ES growth medium component that is required for the ES cell culture, but its optimal concentration has not been well studied. Fluorescent ES cells can be used to study the effect of FBS on ES cell growth and the result can be used to aid the medium design. One day after seeding, the 3-D cell matrices were cultured in ES media with different FBS contents ranging from 0% to 10% (v/v) and the culture fluorescence signals were monitored. As can be seen in FIG. 7, no cell growth was observed when there was no FBS in the medium and cell growth increased with increasing the FBS content from 0% to 3%. However, further increasing the FBS content to 10% did not significantly affect ES cell growth. This study suggests that 1% to 3% FBS would be appropriate for ES cell culture.

Currently, 10% FBS is commonly used. Reducing the FBS content can significantly reduce the medium costs in large-scale cell culture processes.

Figure 8:
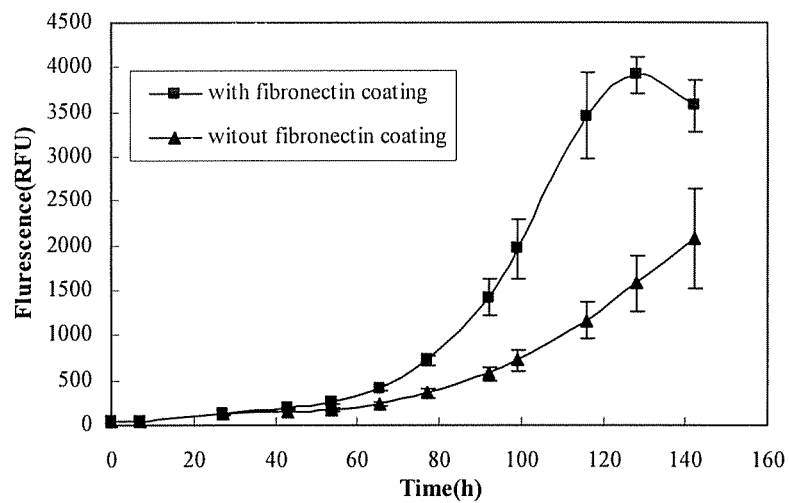
FIG. 8 illustrates ES-GFP cultures used to investigate the effect of fibronectin coating on cell growth. Three samples were with fibronectin coating, while the other three samples were without fibronectin coating. Each point represented the average fluorescence from triplicate samples.
Figure 9:
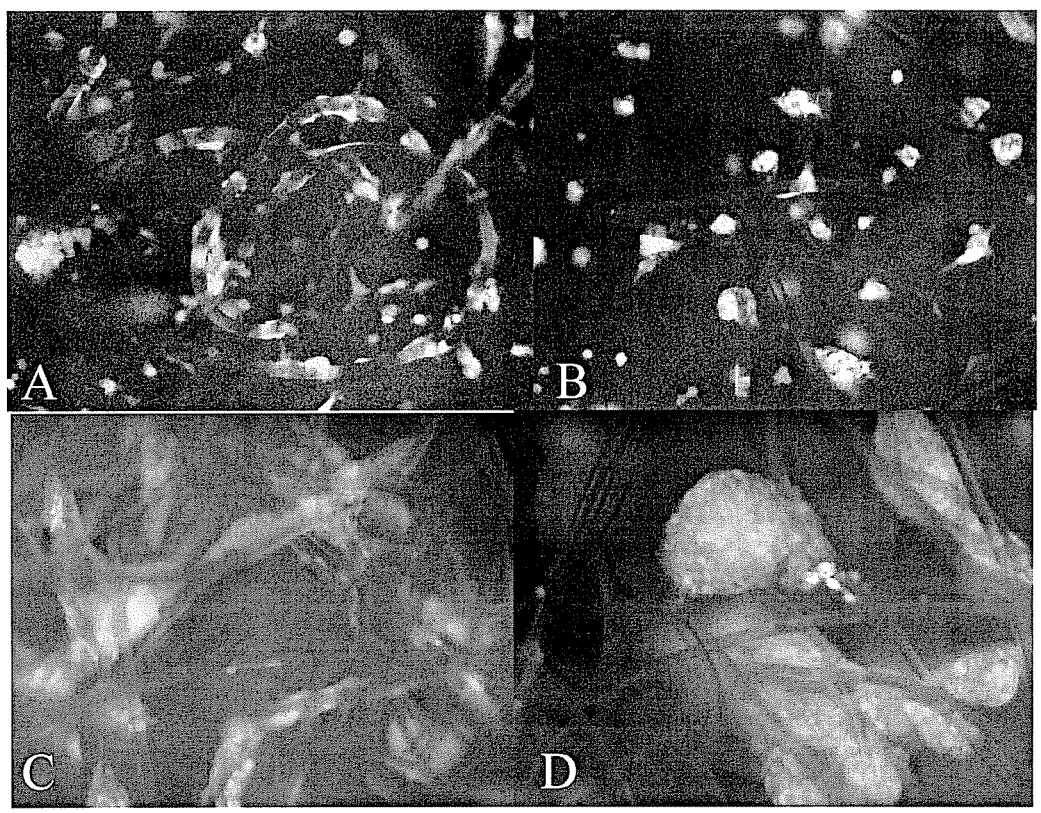
FIG. 9 illustrates fluorescent microscopic images of ES-GFP cells on 3-D scaffolds. A. one day after inoculation with fibronectin coating; B. one day after inoculation without fibronectin coating; C. 4 days after inoculation with fibronectin coating; D. 4 days after inoculation without fibronectin coating. An inverted fluorescent microscope (Nikon Ecllipse TE2000-U) was used for detection.

Similarly, ES-GFP cells were used to study the effects of fibronectin coating of the PET matrix on cell growth. Fibronectin is involved in many cellular processes, one of which is to serve as a general cell adhesion molecule to help cells anchor onto proteoglycan or collagen substrates. Fibronectin is a commonly used extracellular matrix protein to enhance cell adhesion on the tissue scaffold. PET matrices were soaked in 10 μg/ml fibronectin (Sigma Chemical Company, St. Louis, Mo.) for 12 hours before use. The fibronectin-coated matrices were then placed in the growth medium and seeded with ES-GFP cells from the top of the scaffolds. As shown in FIG. 8, a fibronectin coating conferred a distinct enhancement in cell growth. With fibronectin coating, the specific growth rate increased from 0.0335 h$^{-1}$ (doubling time 20.7 h) to 0.0458 h$^{-1}$ (doubling time 15.1 h), a 37% enhancement. Also, cells cultured in the fibronectin-coated matrix reached a maximum fluorescence intensity of 4000 RFU that was ~2.5 times of that without fibronectin coating at 128 h. The much higher fluorescence intensity reading can be partially attributed to better cell adhesion and spreading in the fibronectin-coated matrix, as seen under a fluorescent microscope (see FIG. 9). Cell spreading can also stimulate cell proliferation and contributes to uniform cell distribution in the 3-D matrix, which in turn allowed more light emission from the matrix. It is noted that cells developed different morphologies in these two matrices, with large aggregates formed in the matrix without fibronectin coating (FIG. 9D). The formation of large cell aggregates could add additional mass transfer limitation and further reduce cell growth. The adhesion of cells to PET fibers is important to determine the cell growth in the 3-D matrix.

Example 2

Acute Cytotoxicity

Figure 10:
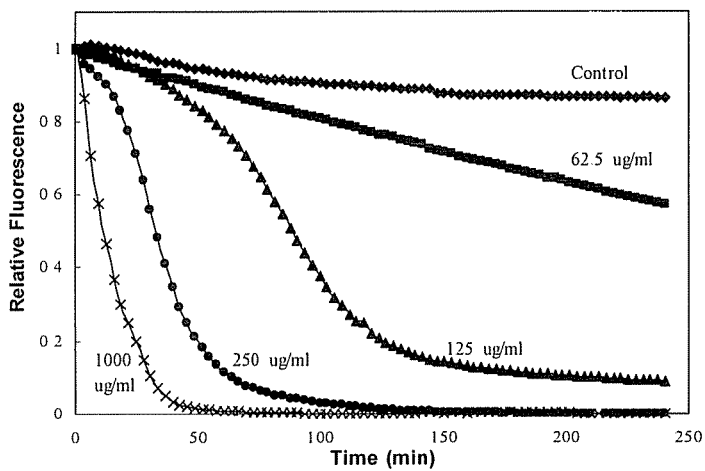
FIG. 10 illustrates acute cellular responses to Triton X-100. A. Relative fluorescence kinetics with different Triton X-100 concentrations. B. Semi-log plot of fluorescence kinetics to calculate $k_d$. C. Correlation between Triton X-100 concentration and $k_d$.
Figure 10:
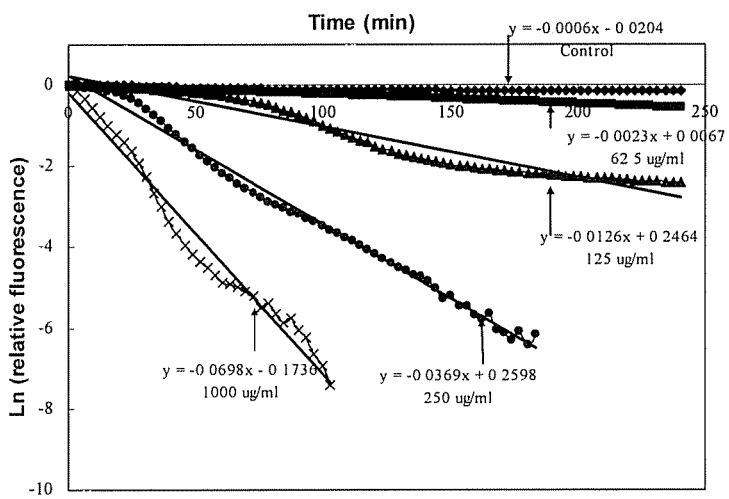
Figure 10:
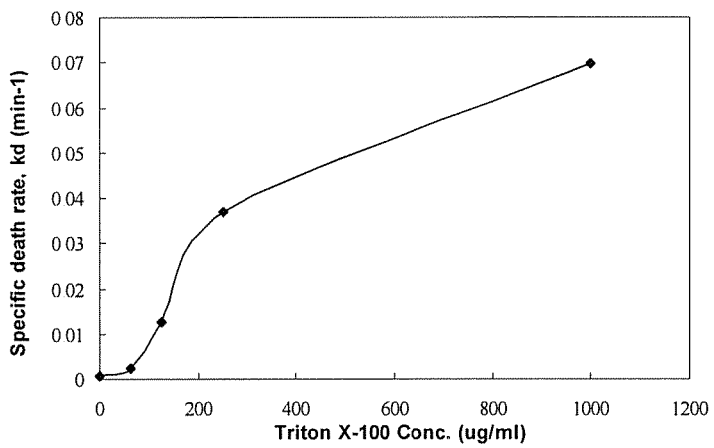

For the live-cell kinetic assays, acute cellular events can be easily characterized with online continuous fluorescence measurements without human intervention. The 3-D cell-based assay system was thus applied to test the response of ES-GFP cells to a surfactant, Triton X-100 (Sigma Chemical Company, St. Louis, Mo.). ES-GFP cells in the 3-D system were cultured to reach a high density with 2000 RFU fluorescence intensity. After applying different doses of Triton X-100, the culture plate was immediately put into the plate reader (Cytofluor Series 4000) at 37° C., with the cycle number set at 80 and cycle time at 3 min. The mixing time before each reading was 10 seconds. As can be seen in FIG. 10, the surfactant caused an acute cell death as indicated by the loss in the culture fluorescence. In general, increasing the surfactant concentration in the medium increased cell death, which followed a first order kinetics as indicated by the linear semi-logarithmic plot (FIG. 10B). Triton X-100 is a non-ionic detergent commonly used to solubilize membrane proteins. The specific death rate $k_d$ at each Triton X-100 concentration can be estimated from the negative slope of the semi-log plots. FIG. 10C shows the correlation between Triton X-100 concentration and the $k_d$ value. The loss in the fluorescence signal for the control experiment without the surfactant was negligible and the slight decrease could be attributed to a slow increase in the medium pH outside the $CO_2$ incubator. GFP fluorescence is marginally affected by the solution pH when it is in the neutral pH range.

Example 3

Drug Effects on ES Cell Growth

One application of the fluorescent cell-based assay is for high-throughput drug screening for cytotoxicity effects. Two weak embryotoxic chemicals, dexamethasone (DM) and diphenylhydantoin (DPH), one non-embryotoxic chemical, penicillin G, and one strong embryotoxic chemical, 5-FU were applied at various concentrations to ES cells grown in 2-D and 3-D at the early proliferation stage (drug exposure one day after seeding the matrices).

Figure 11:
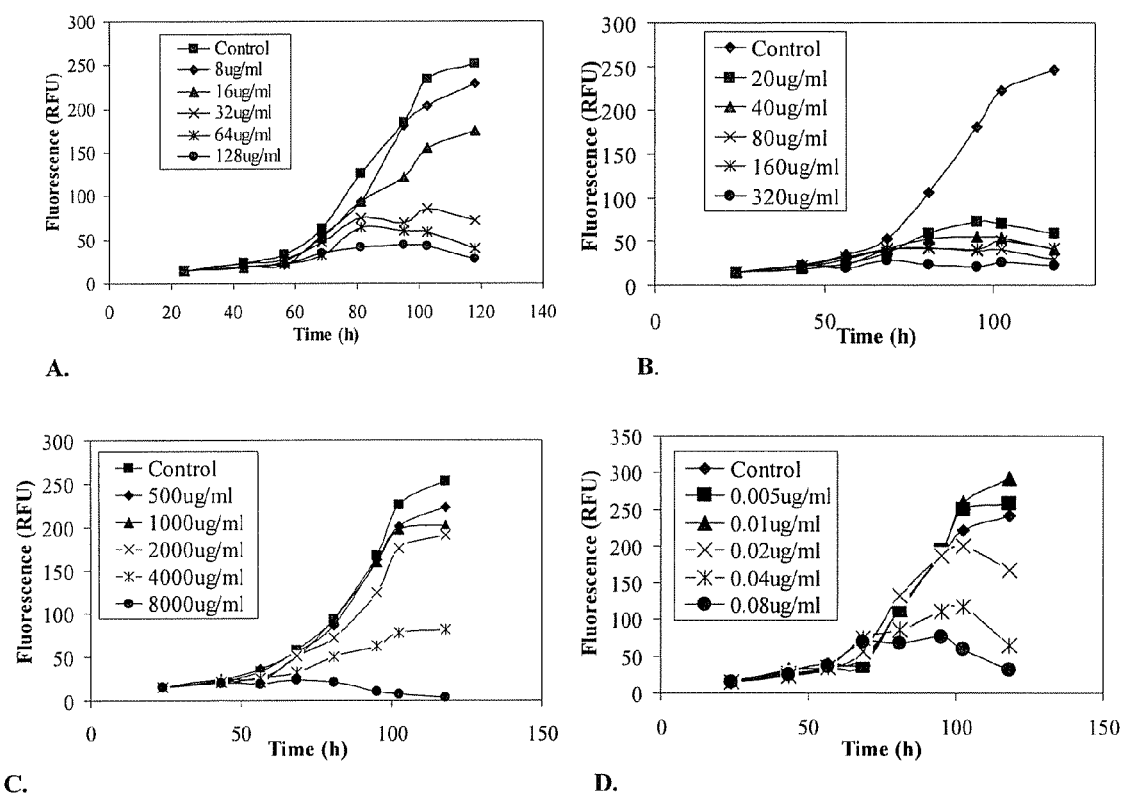
FIG. 11 illustrates fluorescence kinetics with exposure to four embryotoxic reference chemicals in a dose-dependent manner one day after inoculation in 2D cultures. A. DM; B. DPH; C. Penicillin G; D. 5-FU.

The 2-D cytotoxicity assay was performed in 96-well plates by inoculating 5000 cells into each well containing 150 μl of ES medium. The drug was added one day after inoculation. Fluorescent signals were measured twice per day in the culture plates. The fluorescence given by live cells was calculated as the signals obtained after replacing culture medium with the same volume of PBS minus the blanks. As expected, the fluorescence time course data showed the drug effects on ES cell growth: decreasing cell growth as the drug dosage increased (FIG. 11). However, at a low dosage of 5-FU, a higher culture fluorescence was obtained as compared to the control (no drug). This increased fluorescence signal was attributed to the increased specific expression of EGFP instead of a stimulation effect on cell growth. The increased specific GFP expression can introduce a false drug effect. It was also found that cells grown in the presence of 5-FU had a larger cell size (12-14 μm vs. 11 μm). This might be because cell treated with 5-FU (an S-phase drug) stopped DNA synthesis, while cells continued to grow in size.

Figure 12:
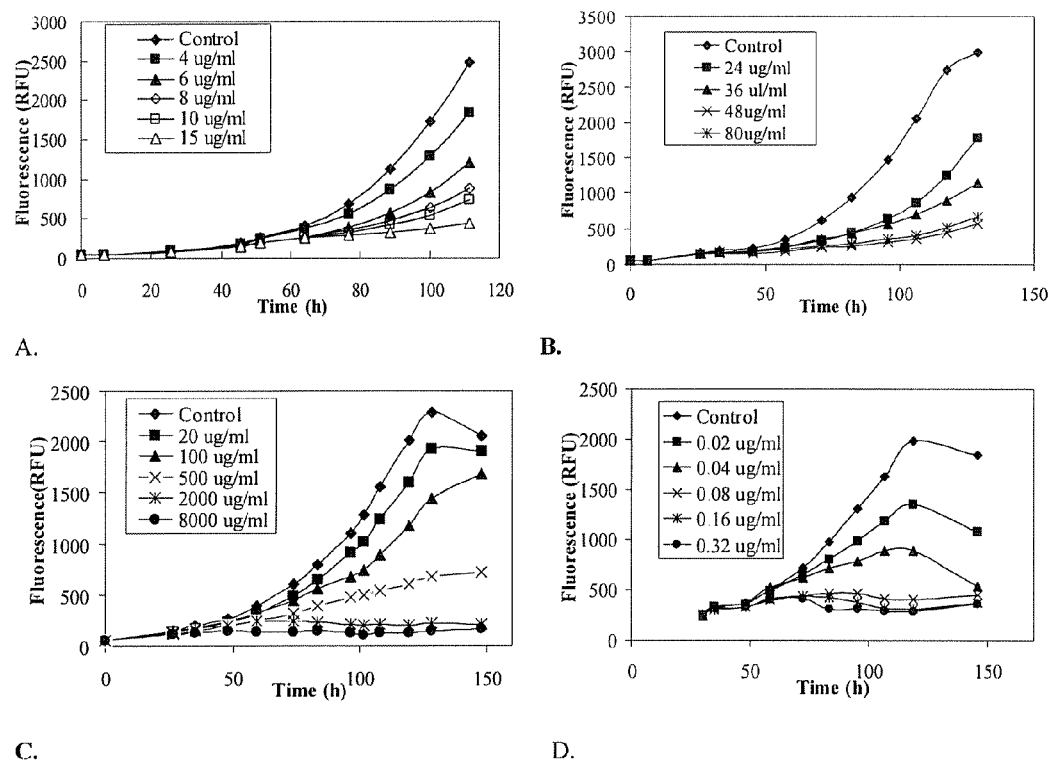
FIG. 12 illustrates fluorescence kinetics with exposure to four embryotoxic reference chemicals in a dose-dependent manner one day after inoculation in 3-D cultures. A. DM; B. DPH; C. Penicillin G; D. 5-FU.

For the 3-D cytotoxicity assay, 25000 cells in 25 μl medium were seeded into each PET scaffold. After 6 h incubation to allow cell attachment, 180 μl medium were added to each well and incubated for another 18 h before transferring the seeded matrix to the center of the microbioreactor chamber containing 3 ml of the ES medium on the modified 96-well plate. The plates were then stacked onto a rotational shaker and put into a 37° C. $CO_2$ incubator. The culture fluorescence was measured twice per day with a Cytofluor Series 4000 plate reader. Fluorescence signals from live cells were calculated as the values from the central well of the bioreactor minus the background from the surrounding medium and scaffold. As expected, cell growth was increasingly inhibited by these drugs as their dosages increased (FIG. 12). It is noted that the 3-D proliferation assay did not show any false drug effect caused by changed specific EGFP expression as seen in the 2-D culture with 5-FU.

Figure 13:
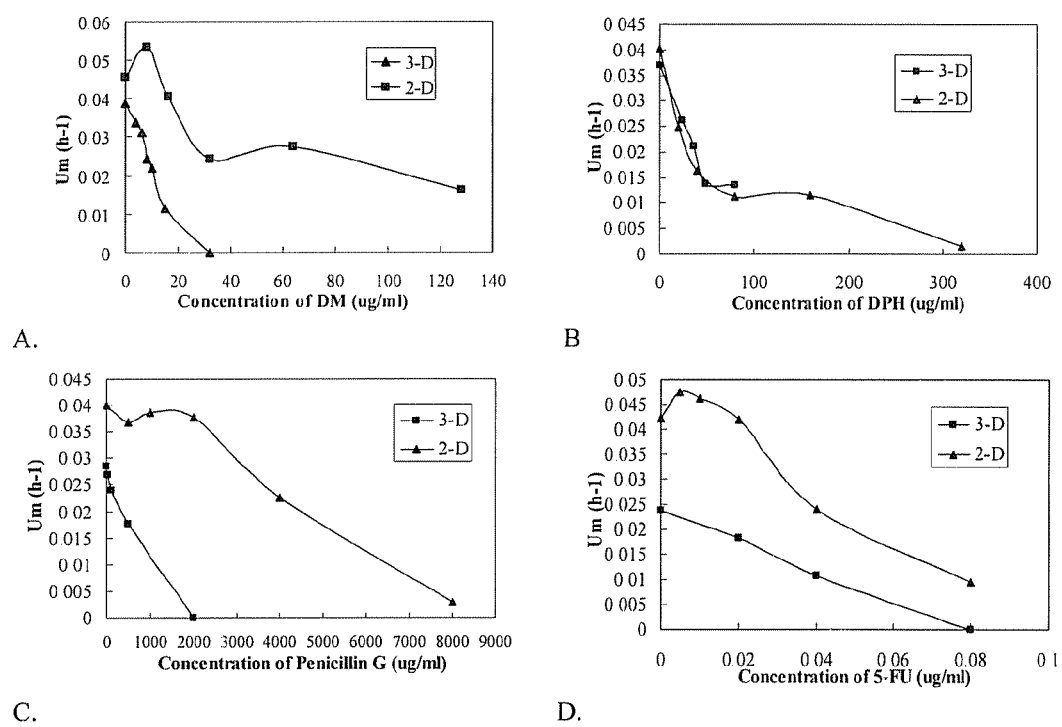
FIG. 13 illustrates a correlation between chemical concentration and $\mu_m$ in both 3-D and 2-D systems. The cytotoxicity $Ig_{50}$ of chemicals was expressed as the chemical concentration causing 50% inhibition of $\mu m$. A. DM; B. DPH; C. Penicillin G; D. 5-FU.

All four drugs show considerable cytotoxicity in both 2-D and 3-D cultures. FIG. 13 shows the drug dosage effects on the specific growth rate in 2-D and 3-D cultures. Cytotoxicity is commonly evaluated by using $IC_{50}$ (50% growth inhibition), TGI (total growth inhibition), and $LC_{50}$ (50% cell killing), but these parameters are not always available or suitable to use. With the exponential-phase specific growth rate data, the cytotoxicity of various chemicals can be better evaluated by their $Ig_{50}$ values defined as the concentration of the chemical causing 50% reduction in the exponential-phase specific cell growth rate. Table 1 compares the cytotoxicity test results from the 2-D and 3-D culture assays and the results from similar embryonic stem cell tests reported by ZEBET and ECVAM. The $Ig_{50}$ values from the 3-D culture assays are generally lower than those from the 2-D culture assays and the $IC_{50}$ values from embryotoxicity test previously reported. For DM and Penicillin G, $Ig_{50}$ in 2-D were 3 and 6 times of $Ig_{50}$ in 3-D, respectively. The difference of 5-FU cytotoxicity in 3-D and 2-D was not significant. $Ig_{50}$ of DHP in 2-D and 3-D was similar but lower than the results from embryotoxicity test. Overall, the 3-D fluorescent ES cell proliferation assay is more sensitive than 2-D assay and other embryonic stem cell tests reported by ZEBET and ECVAM.

TABLE 1

Cytotoxicity of four embryotoxic reference chemicals estimated from various assays.

| | 3-D cultures $Ig_{50}$ (μg/ml) | 2-D cultures $Ig_{50}$ (μg/ml) | ZEBET $IC_{50}$ (μg/ml)[a] | ECVAM $IC_{50}$ (μg/ml)[a] |
|---|---|---|---|---|
| DM | 11.5 | 32 | 37 | 51 |
| DPH | 39 | 30 | 102 | 195 |
| Penicillin G | 750 | 4500 | 2100 | 2000 |
| 5-FU | 0.035 | 0.045 | 0.09 | 0.065 |

[a]ZEBET: Center for Documentation and Evaluation of Alternative Methods to Animal Experiments; ECVAM: European Centre for the Validation of Alternative Methods Example 4

Drug Effects on 3-D ES Tissues

Culture organization can modulate cellular molecular mechanisms and result in changes of cell cycle progression, which further alter the responses of individual cells to chemicals. In both tumors and normal tissues in vivo, most of cells are in a quiescence state with a very small proportion of actively dividing cells. Multicellular tumor spheroids have been shown to be better 3-D in vitro models that can reflect the tumor pathophysiological situation and show much more similar responses to external stimuli to their in vivo counterparts. Experiments to assess the differences between monolayer cells and multilayer cells showed a reduction of cells in S-phase in multilayer cultures accompanied by a change of cell-cycle specific protein expression and nucleotide pools. Using BrdU-PI dual-staining confocal laser scanning microscopic study, it is known that long term cultures have fewer cells in S-phase than the 3-day culture in PET scaffolds accompanied with decreased expression of proliferating marker cyclin B1 and increased expression of quiescence marker $p27^{kip\ 1}$. Due to the different cell cycle specificity of chemicals, high-density cells such as tumor spheroids or tissue constructs in PET scaffolds can be expected to show different levels of resistance compared to conventional cultures with high proliferating cells.

Figure 14:
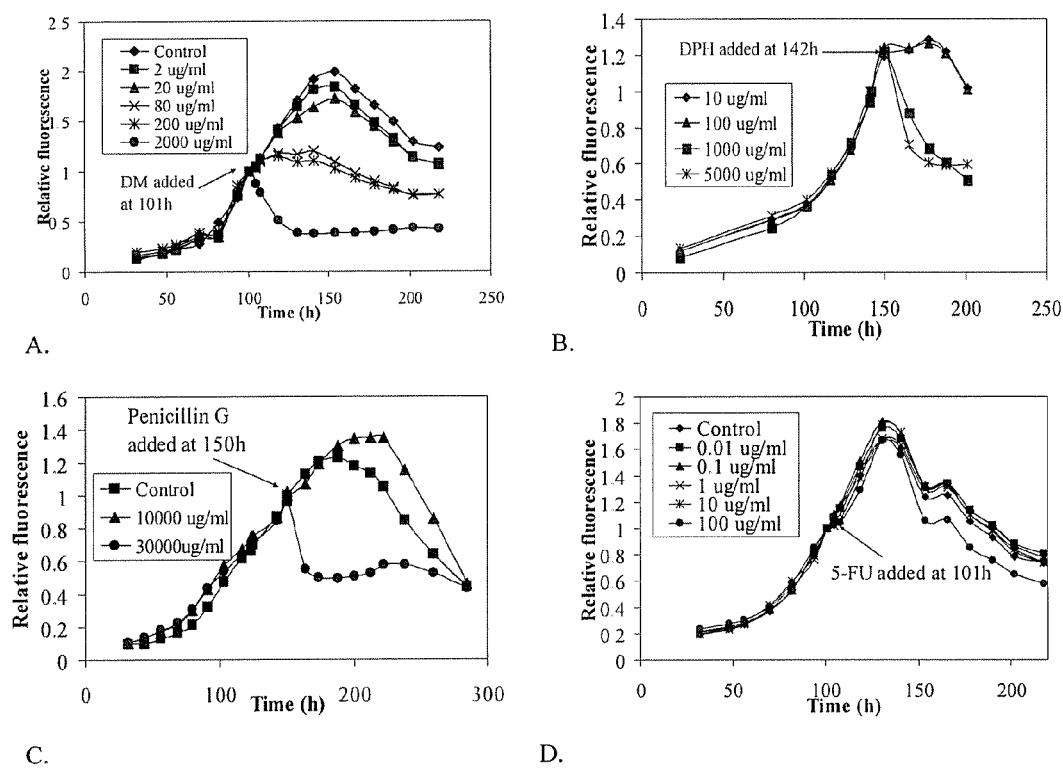
FIG. 14 illustrates fluorescence kinetics with exposure to four embryotoxic reference chemicals in a dose-dependent manner in 3-D tissue constructs. Relative fluorescence intensity normalized against the signal at the time point of chemical addition. A. DM; B. DPH; C. Penicillin G; D. 5-FU.

The effects of various drugs on ES cells grown in 3-D after reaching a high cell density (exposure four or six days after seeding the matrices) were studied and the results are shown in FIG. 14. $EC_{50}$ (the concentration required for obtaining 50% of a maximum effect) is used to evaluate a drug's cytotoxicity effect on a high-density 3-D cell or tissue construct. Here, if the elimination of cells is considered as the maximum effect of a chemical, an $EC_{50}$ is not always reached. A similar problem was found that a chemical could not kill most of cells even when the chemical reached the saturation concentration in the medium. For this case, the maximum effects were defined as the fluorescence reduction caused by the saturation concentration (DM and DPH) or a very high dose compared to doses used in 2-D assays (Penicillin G and 5-FU). In addition, it was also noticed that maximal effects changed along with time, so the time point with the largest value of the maximal effects was used for cytotoxicity definition. Rf (resistance factor) is defined as the ratio between $EC_{50}$ and $Ig_{50}$. Rf close to 1 shows that the cytotoxicity of a chemical to 3-D high density cells is similar to low density cells, while a high Rf means a large difference of cytotoxicity between these two cultures.

Despite a very high dose used (up to 2857 times of $Ig_{50}$), cells in tissue constructs were almost insensitive to 5-FU. The extent of cell kill at the maximum dose of 5-FU was only 20%, much lower as compared with the previous experiment. Because of the lack of effectiveness, $EC_{50}$ of 5-FU was not meaningful. In contrast, DM, DPH, and Penicillin G showed considerable cytotoxicity in ES tissue constructs, with the extent of cell kill 80.9%, 52.2% and 62.3% respectively (Table 2).

TABLE 2

Cytotoxicity and the extent of cell kill upon the exposure of ES cells to embryotoxic reference chemicals in 3-D high-density cell cultures.

| | $EC_{50}$ (μg/ml) | Extent of cell kill | Rf |
|---|---|---|---|
| DM | 65 | 80.9% | 5.7 |
| DPH | 600 | 52.2% | 15.4 |
| Penicillin G | 23000 | 62.3% | 30.7 |
| 5-FU | N/A | 20.0% | >1000 |

The drug resistance of ES cells to all four chemicals increased in the 3-D high density cultures when compared to 2-D monolayer and 3-D low density cultures (see Table 1). Although Rf values were different for the first three chemicals, in general, these chemicals could cause sufficient cytotoxicity at a decent dose (less than 50 times higher than those used in 3-D low density). However, 5-FU had no significant effect even at a high concentration of 100 μg/ml, over 2000 times higher than the dose used in assays with low density cells. In other words, 5-FU was almost non-effective to the tissue constructs of ES cells. 5-FU is small water-soluble molecule and easy to penetrate into tissues. Several hours were enough for it to diffuse through more than 100 μm thick solid tissue. Therefore, 5-FU seems able to reach each cell in tissue constructs with certain amount and the penetration of this chemical is not supposed to be the main obstacle for effectiveness. Considering the S-phase specificity of 5-FU and the reduced S-phase cells in PET 3-D long term cultures, we can suspect that in comparison with 2-D and 3-D low density cells, the 3D tissue constructs have a different cell cycle progression, which can cause various cellular responses to S-phase specific or non S-phase specific chemicals.

Example 5

Promoters for Specific Cytotoxicity Studies

Figure 15:
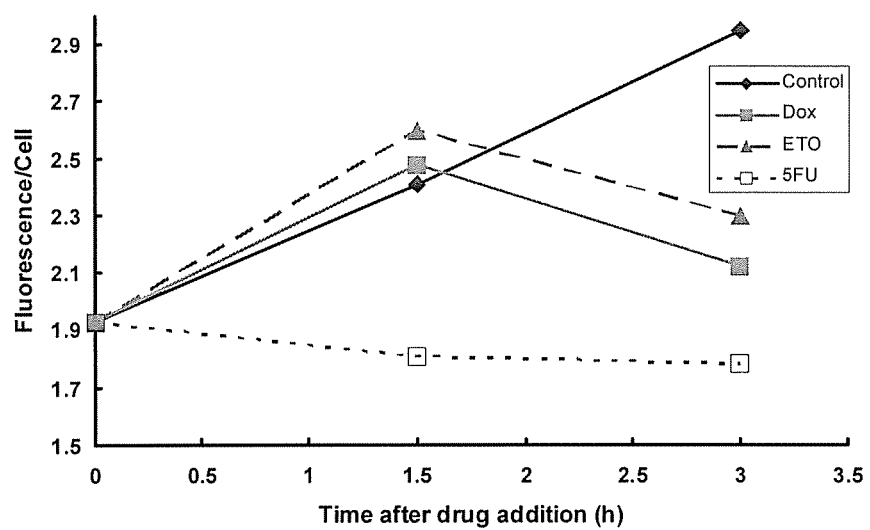
FIG. 15 illustrates the effects of different drugs on inhibiting cell growth. The acute cytotoxicity response was dependent on the type of drug action on the cells. The response was immediate for S-phase specific drug, while there was a time lag in the cell response for drugs that are G2/M phase specific or not cell-cycle specific.

The constitutive human CMV immediate early promoter is S-phase specific, i.e. sensitive when cells are proliferating. Therefore, for acute cytotoxicity assay, the rate of GFP loss will depend on the specific cell-cycle arresting chemotherapeutic drugs, and it was verified by cell cycle analysis. FIG. 15 shows a significant difference in the pattern of fluorescence decrease when applying 5-fluorouracil (5-FU), which is an S-phase specific agent, etoposide (G2/M phase specific) and doxorubicin (cell cycle non-specific). Therefore, it is also possible to distinguish the toxicological effect on cell cycle stage by the culture fluorescence kinetics.

Besides a CMV promoter, a cytotoxicity study can be extended to using different (specific) promoters and/or biomarkers in the assay. Using different promoters and biomarkers can expand the screening capability based on different genetic and cellular responses; thus, allowing for multiplex testing and biospecific detection/screening. Besides ES cells, other mammalian cells of different tissue types also can be cloned for EGFP expression.

For cytotoxicity, there are other mechanisms that also can be used in cell-based assays. For example, cell damage may occur when there is oxidative stress. In many detoxification enzyme genes there is an antioxidant response element (ARE). Glutathione-S-transferase (GST) is an ARE that has a minimal promoter to respond to oxidative stresses. Human cytochrome P450 1A1 (CYP1A1) promoter, which is down-regulated under oxidative stress, can be used for studying cell regulation driven by oxidative stress. Cellular immune responses are often activated by cytokines. Interleukin-4 (IL-4) promoter conjugated with yellow fluorescence protein can be used to study the early activation of lymphocyte subsets. The expression of immediate-early response genes can also serve as an endpoint for toxicity studies. Elevated gene expression of the immediate-early response c-fos is a sensitive indicator for various cell stresses, including oxidative stresses, apoptosis, and inflammation, etc. GADD153 is an early alert gene that is expressed after DNA damage, which can be another mechanism for studying the cytotoxicity. The promoters for these assays can be human originated in order to ensure that relatively authentic responses can be obtained. In general, the promoters are conjugated with reporter proteins that have different fluorescent colors. For example, each cell type can be transfected with CMV promoter gene as a proliferation marker and another mechanistic promoter gene based on the characteristic responses of that kind of cells to xenobiotics with a different reporter.

Example 6

Colon Cancer Model for Drug Screening

Figure 16:
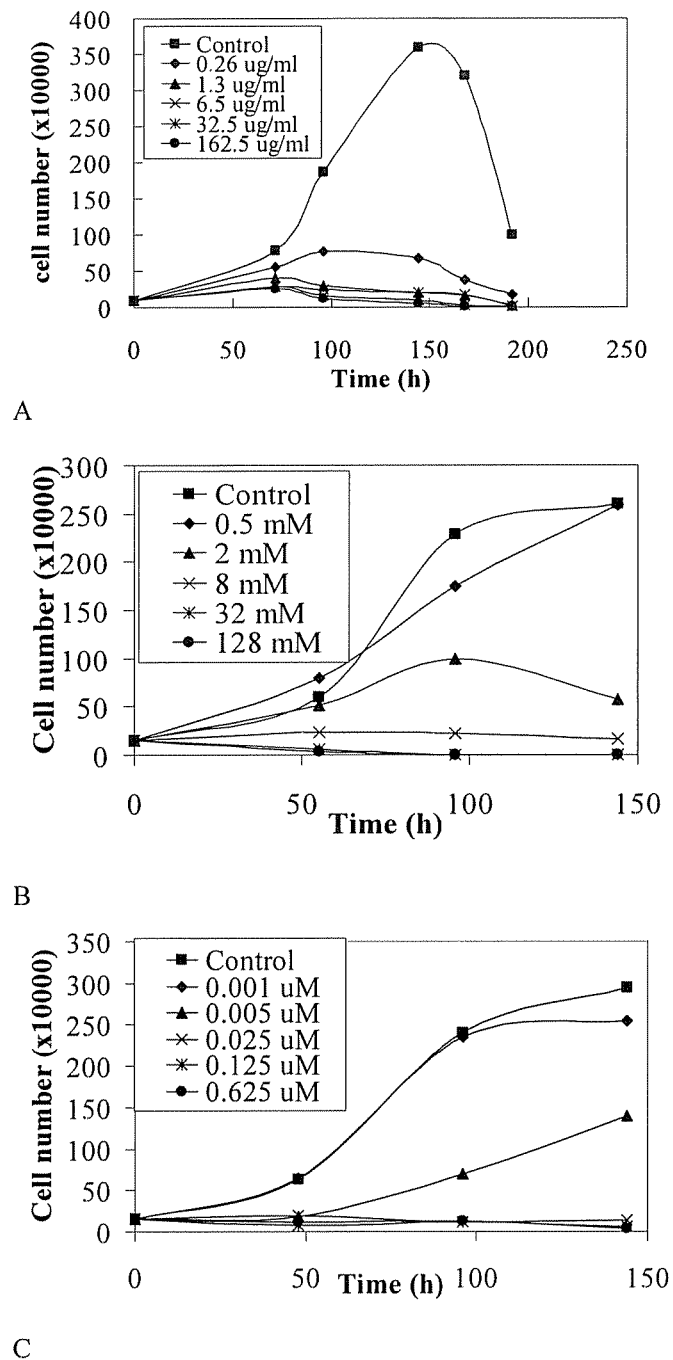
FIG. 16 illustrates the growth kinetics quantified by cell counting with exposure to three chemicals in a dose-dependent manner one day after inoculation in 2-D colon cancer cell cultures. A. 5-FU; B. sodium butyrate C. gemcitabine.
Figure 17:
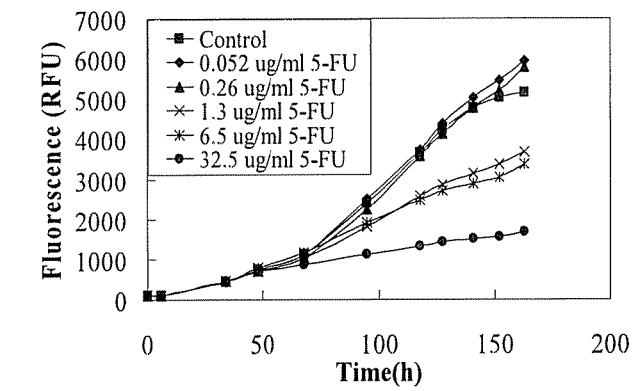
FIG. 17 illustrates the fluorescence kinetics with exposure to three chemicals in a dose-dependent manner one day after inoculation in 3-D low density colon cancer cell cultures. A. 5-FU; B. sodium butyrate C. gemcitabine
Figure 17:
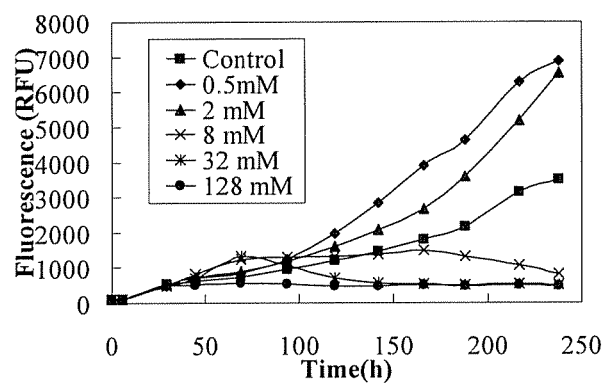
Figure 17:
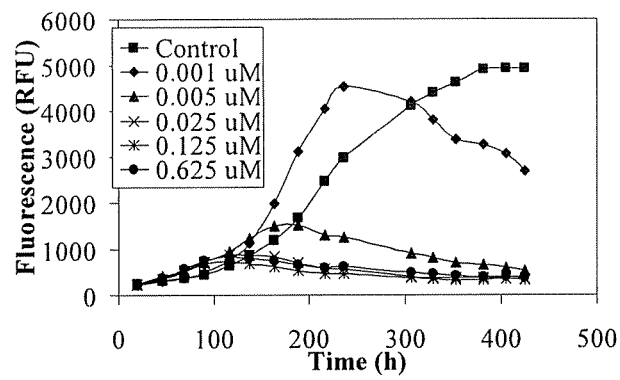
Figure 18:
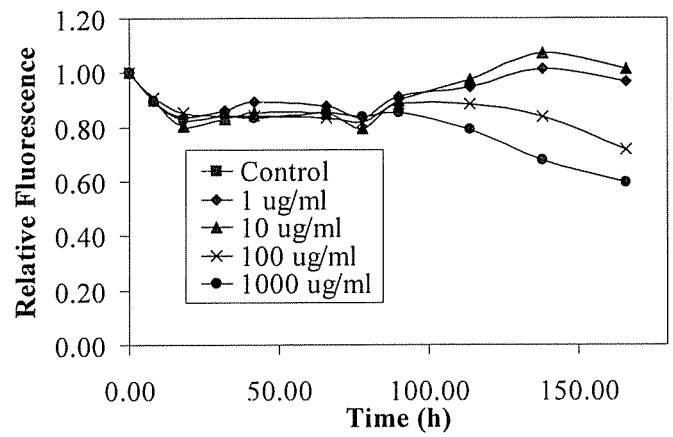
FIG. 18 illustrates the fluorescence kinetics with exposure to three chemicals in a dose-dependent manner in 3-D high cell density tissue constructs. A. 5-FU; B. sodium butyrate C. gemcitabine.
Figure 18:
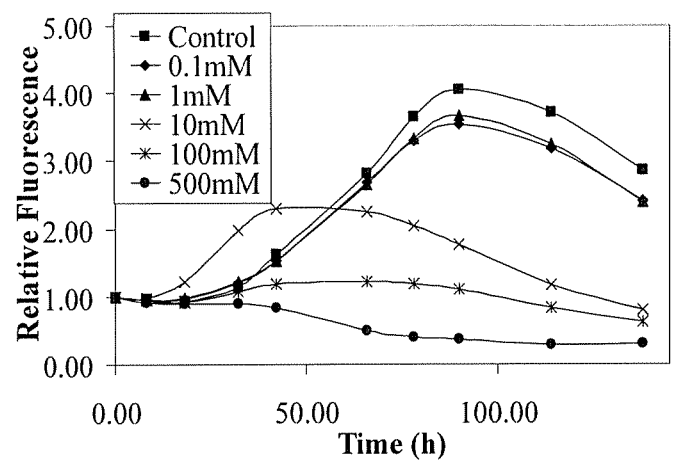
Figure 18:
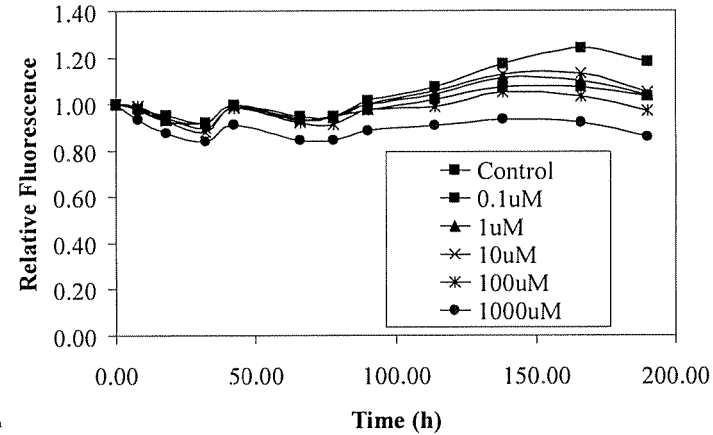

Colon cancer is the third most frequently occurring cancer in the US and causes large numbers of deaths, second only to lung cancer. Treatment of progressed colon cancer involves surgical extraction combining chemotherapy and immunotherapy. The survival rate of colon cancer patients is only 55% due to the low effectiveness of these therapies. 5-Fluorouracil has been widely used during the past few decades to treat colon cancer, but more and more new drugs emerged. Butyric acid is a biological response modifier (BRM) and it acts synergistically with 5-FU against colorectal cancers by decreasing thymidine kinase mRNA. As a BRM, it can also increase cell specific productivity at the expense of inhibiting cell growth. In this example, HT-29-GFP, colon cancer cells (HT-29) stably expressing EGFP were exposed to 3 chemicals: 5-FU, sodium butyrate, and gemcitabine in 2-D cultures (FIG. 16), 3-D low density cultures (FIG. 17) and 3-D tumor-like constructs (FIG. 18). Because all of these 3 chemicals could increase cell specific fluorescence, cell counting instead of fluorescence was used for quantification in the assays with 2-D cultures. For assays performed in 3-D cultures, it was found that low doses of chemicals could always result in higher fluorescence compared to the control, while high doses of chemicals decreased the fluorescence. In this case, the cytotoxicity of a chemical in 3-D cultures was defined as a concentration range of the chemical. The minimum limit was the largest dose which could result in the fluorescence higher than the control and the maximum limit was the smallest dose which made the fluorescence lower than the control.

The results of anticancer drug study showed that an assay with tumor-like constructs was a better high-throughput alternative in drug screening than cell proliferation assays (exposure of chemicals to 2-D cultures and 3-D low cell density) and significantly different cellular responses also existed between the proliferation assays and the tumor-like assays (exposure of chemicals to 3-D high density cells) (Table 3). Colon cancer cells with high density (tumor morphology) seem totally resistant to gemcitabine, which coincides with known results. Gemcitabine is an S-phase specific drug. Colon cancer multi-layers contain less S-phase fraction than monolayers, thereby contributing to part of the resistance to gemcitabine in these solid tumors. At this point, sodium butyrate is much better. The resistance to sodium butyrate in tumor-like structure was only 10 times that in 3-D low density cells. Moreover, sodium butyrate began to cause significant fluorescence changes only one day after drug addition. The resistance to 5-FU in 3-D tumor-like structure was about 50 times of that in 3-D low density cells. Meanwhile, 5-FU did not affect the fluorescence kinetics until four days after drug addition. In general, sodium butyrate was found to be more effective than 5-FU in tumor-like model when multicellular resistance and the time to take effects were considered. When comparing the toxicity of these two chemicals on 2-D cultures, it was found that HT-29 were several times more resistant to both drugs than ES cells, which means that neither of them has the selectivity to kill cancer cells instead of ES cells. However, the conclusion is contrary when toxicity was compared in ES tissue-like structure and HT-29 tumor-like structure. ES tissue-like structure was more resistant to 5-FU than HT-29 tumor-like structure, while for sodium butyrate, the selectivity is adverse. The better selectivity of 5-FU indicated here might be part of the reason why 5-FU remains the most widely prescribed agent for the treatment of colorectal cancer for the past 50 years. In this case, assays with high density cells could be used to test the selectivity of different chemicals as the guideline for the removal of poor drug candidates.

TABLE 3

Different HT-29-GFP cultures for monitoring cytotoxicity of drugs.

| | | Sodium butyrate (mM) | 5-FU (μg/ml) | Gemcitabine (μM) |
|---|---|---|---|---|
| Proliferation assays | 2-D with cell counting($Ig_{50}$) | 2 | <0.26 | 0.005 |
| | 2-D with fluorescence$^a$ | 8-32 | 0.052-0.26 | 0.625 |
| | 3-D with fluorescence$^a$ | 2-8 | 0.26-1.3 | 0.001-0.005 |

TABLE 3-continued

Different HT-29-GFP cultures for monitoring cytotoxicity of drugs.

| | Sodium butyrate (mM) | 5-FU (μg/ml) | Gemcitabine (μM) |
|---|---|---|---|
| Tumor-like response assays[b] (drug added at high density) | 10-100 (about 10 times more resistance; fluorescence changed one day after drug adding) | 10-100 (about 50 times more resistance; fluorescence changed 4 days after drug adding) | >1000 (more than 1000 times more resistance; almost non-effective) |

[a]cytotoxicity was defined by the lowest concentration of the drug which could cause significant difference of fluorescent kinetics in comparison with the control.
[b]compared with the results from 3-D proliferation assays.

Example 7

Microfluidic Bioreactor Array for Cell-Based Assays

In this example, a microfluidic bioreactor array for carrying out perfusion 3-D tissue culture in a high-throughput fashion is illustrated. The polymeric device has a four-times-four microbioreactor array (see FIG. 3B,C), of which the individual wells contain PET fibrous matrix as the tissue engineering scaffolds. The packaging of the device is facilitated by a frame-assisted assembly (FAA). Cell proliferation is quantified using fluorescence intensity measurement in a microplate reader, allowing high-throughput data acquisition. The tissues are optically accessible for measurement and monitoring using microscopy during the whole culture process. In addition, post-culture analyses of the cells are also easily available due to the direct accessibility of the cells enabled by the FAA packaging. Not only does this platform technology allows the test of a drug for its effects on cells at different concentrations, but also different tissue engineering scaffolds can be screened for best performance, and co-culture of various relevant cell types can be utilized to study cell-cell interactions in 3D perfusion culture.

Device Fabrication

The microfluidic bioreactor array had two layers made of poly(dimethylsiloxane) (PDMS) with features facing each other and in close contact. Each layer was designed to specifically serve as part of a network of microfluidic channels or wells for medium flow or cell culture. The PDMS pieces were fabricated using photolithography and replica molding. The process starts with spin coating a thin layer of photoresist SU-8 100 on a silicon wafer. The designed depth of the cell culture well was 1 mm, deciding that each layer to be about 500 μm in thickness. However, the available protocol for spin coating only allowed a thickness of up to around 400 μm. Therefore, a modified procedure was employed for rendering a desirable thickness of the SU-8 coating, where after a spin coating of a 150 μm layer followed by soft baking, another spin coating following the 150 μm procedure was used, resulting in a thickness close to 500 μm. After soft baking, the photoresist was exposed to UV and then developed to be photolithographically patterned with features of design. The masters for the top and the bottom layers were both made using this procedure. PDMS prepolymer and curing agent were mixed by a ratio of 10:1, and poured onto the masters before polymerization on a 70° C. hotplate for 2 hours. Then the PDMS layers were cut and peeled off from the wafers.

Frame Assisted Assembly (FAA)

For packaging, a set of frames made of polycarbonate was designed, on which perforations were made in alignment with cell culture wells. After depositing tissue culture scaffold into each well on the bottom PDMS layer, the top and bottom frames were used to clamp the two PDMS pieces in between by screws. The fluid ports were made using needles of gauge 16 (B-D) which were blunted and blended for connections between the microchip and the macroworld. PDMS was employed for gluing and sealing of the fluidic ports.

Cell Line and Media

A human colon cancer cell line HT-29 (ATCC: HTB-38™) was maintained in Dulbecco's Modified Eagle's Medium (DMEM, Gibco) supplemented with 10% fetal bovine serum (FBS, Gibco) in a cell culture incubator at 37° C. with 5% $CO_2$. The HT-29 cells were transfected with PEGFP-N3 (Clontech) using Lipofectamine 2000 (Invitrogen), with which enhanced green fluorescent protein (EGFP) was expressed under the control of cytomegalovirus (CMV) promoter, a strong constitutive promoter. Then cells were diluted and seeded in a 96 well plate at around 5 cells per well. One green fluorescent colony was isolated and expanded in the absence of selective pressure geneticin (G-418, Gibco). The stability of the transfected cell line was verified by FACS-Calibur (B-D) (>97%) compared to the negative control. Data showed that the growth rate of the transfected cells was not affected by EGFP expression.

Tissue Culture Scaffold

Treated nonwoven polyethylene terephthalate (PET) fibrous matrices (diameter: ~20 μm; density: 1.35 g/cm$^3$) was used as the tissue engineering scaffold. PET matrices were compressed under 30 kPa at 120° C. for 60 min, resulting in matrices about 1.0 mm thick with porosity of about 0.85 and average pore size of about 45 μm. Then the PET fibers were soaked in solution of 1% (v/v) $Na_2CO_3$ and 1% (v/v) Tween-20 which was heated to 60° C. and maintained for 30-60 min. After rinsing with distilled water, PET matrices were boiled in 1% (v/v) NaOH solution for 30-60 min. Then after thorough rinsing, the matrices were kept in water.

Quantitative Analysis of Cell Proliferation

Cell proliferation was quantitatively monitored in a high-throughput manner by using a fluorescence microplate reader, TECAN GENiosPro™. The four times four microbioreactor array had a unique layout, so that a plate definition should be made before fluorescence intensity measurement. A transparent cover for a multi-well plate was modified as a holder of the microchip for loading onto the microplate reader (see FIG. 3E). Each fluidic port was capped with short Tygon S-50-HL tubing with one end heat-bonded to close the system, preventing contamination. By using plate definition scanning at an excitation wavelength of 485 nm and emission 535 nm, the "plate" was custom-defined, so that fluorescence intensity in each well of the microchip could be measured as simple as using a commercially available 96 well plate. To test the efficacy of the plate definition, Fluorescein (Sigma) solution of a series of concentrations was dispensed into the wells of the microbioreactor array, and fluorescence intensity was measured at 485 nm excitation and 535 nm emission using the specific plate definition scheme in the microplate reader. Similarly, the correlation between fluorescence intensity and cell number in 3-D tissue engineering scaffold was also studied, which formed the basis for the quantitative analysis of cell proliferation in the microbioreactor array.

Cell Seeding

Before cell culture, the PET matrices were cut to small square patches (2.5 mm×3 mm) and then soaked in water and sterilized in an autoclave at 121° C. for 15 min. After cooling to room temperature, each patch was put in a well of a 384 well plate and the water within the matrix was sucked out using pipette. Then the PET matrix was immersed in 20 µL, fetal bovine serum (FBS) and kept sterile in a cell culture incubator overnight to further increase its cell attachment potential due to the abundant presence of attachment factors in FBS. HT-29 cells expressing EGFP were trypsinized and suspended in the maintenance media. 6 µL, of the cell suspension were seeded into each PET scaffold gently. Then the 384-well plate was put into the incubator, allowing the cells to attach to the matrix. Approximately 6 hours later, each seeded scaffold received 30 µL, media to support static cell culture in the matrix overnight. Then each seeded scaffold was transferred gently to a new well on the same 384-well plate, which was followed by fluorescence intensity measurement in the microplate reader at 485 nm excitation and 535 nm emission. The scaffolds with similar fluorescence intensity were selected and transferred to the wells in the middle two rows of the microbioreactor array. The first and the last rows of wells were filled with unseeded scaffolds as controls which had the same dimensions and treatments as the seeded scaffolds only without the inoculation. Then the device was packaged with the FAA method for batch and perfusion culture experiments.

Static Batch Culture

Figure 19:
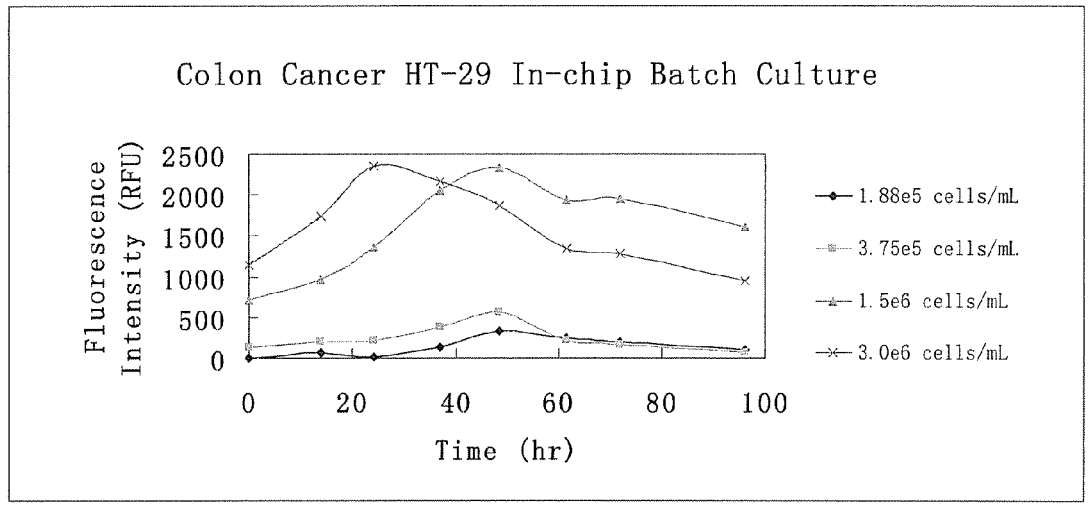
FIG. 19 illustrates the batch kinetics of HT-29 colon cancer cells expressing EGFP cultured in 3-D matrices in a 4×4 microbioreactor array. Seeding density affected the growth of cells in a "to be or not to be" mode, with a threshold value around $10^6$ cells/mL. There was a growth limitation due to the depletion of nutrient.

HT-29 cells expressing EGFP were seeded at a series of different densities ($1.88 \times 10^5$, $3.75 \times 10^5$, $1.5 \times 10^6$ and $3.0 \times 10^6$ cells/mL) and packaged with the FAA method. The packaged device with seeded cells was incubated in a $CO_2$ incubator. The fluorescence intensity was measured in the microplate reader twice a day for monitoring the proliferation of cells for over 6 days. As can be seen in FIG. 19, the culture with low seeding densities (less than $1 \times 10^6$ cells/mL) failed to proliferate, probably due to the little attachment of the cells at low densities to the fibrous matrix. For the culture with seeding densities above $1 \times 10^6$ cells/mL, cell growth was observed with the increase of fluorescence intensity from the increased constitutive expression of EGFP by proliferating cells. However, there was a growth limit in the static batch culture, and fluorescence intensity dropped after less than 2 days, indicating that the number of viable cells decreased as well. As expected, the very limited amount of media failed to support cell growth in long term, suggesting that perfusion culture, which feeds nutrient and removes waste continuously, is more feasible for bioreactors of such small volumes and with cells at high densities than static batch culture.

Perfusion Culture

Figure 3:
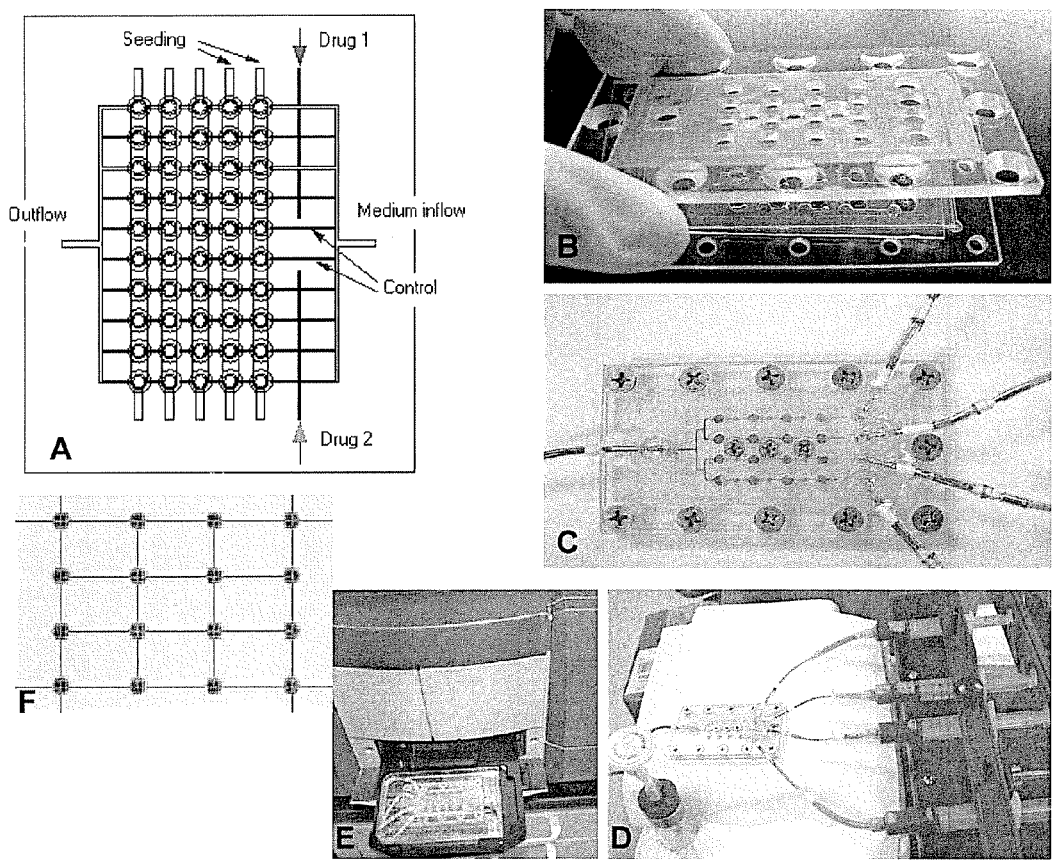
FIG. 3 illustrates a microbioreactor array fabricated on a polymer plate with microfluidic channels connecting microwells for continuous medium perfusion. Microwells can be read by a plate reader with defined scanning positions. A. Microfluidic bioreactors array (5×10) with common medium inlet, common outlet, and cell seeding and drug infusion ports with on-chip dilution capability. B. A microfluidic bioreactors array (4×4) before assembled; C. The microbioreactors array after assembling has four separate medium inlets and one common outlet. D. The microbioreactors connected to syringe pumps; E. The microbioreactors array placed on the plate reader's carrier; F. Position definition generated for the 4×4 microbioreactors array to be read in the plate reader.
Figure 4:
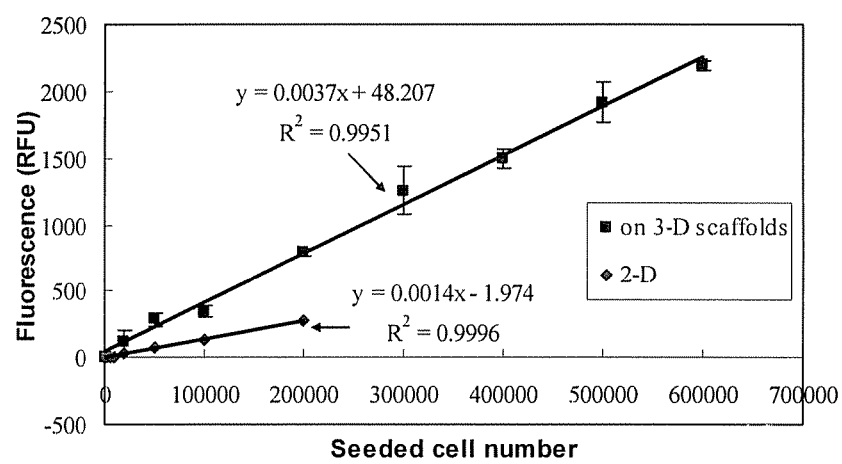
FIG. 4 illustrates that fluorescence intensity from ES-GFP cells is proportional to cell number either in PBS suspension or on 3-D scaffolds. Each point represents the average fluorescence intensity from triplicate samples minus the average fluorescence intensity of blanks. The blanks for suspension are the fluorescence from the same volume of PBS without cells. The blanks for 3-D consist of the fluorescence signals from the same volume medium and scaffolds without cells.
Figure 5:
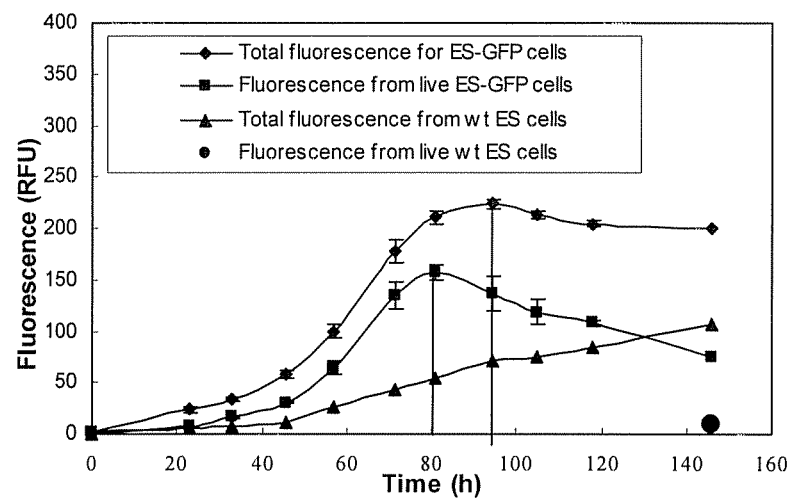
FIG. 5 illustrates a significant difference between the total fluorescence and the fluorescence given by live cells for the ES-GFP cells and the wild type (wt) ES cells. In the first two curves, each point represents the average fluorescence intensity from triplicate samples minus the blank of medium or PBS. In the third curve, each point represents the fluorescence intensity from one sample minus the blank of medium.
Figure 6:
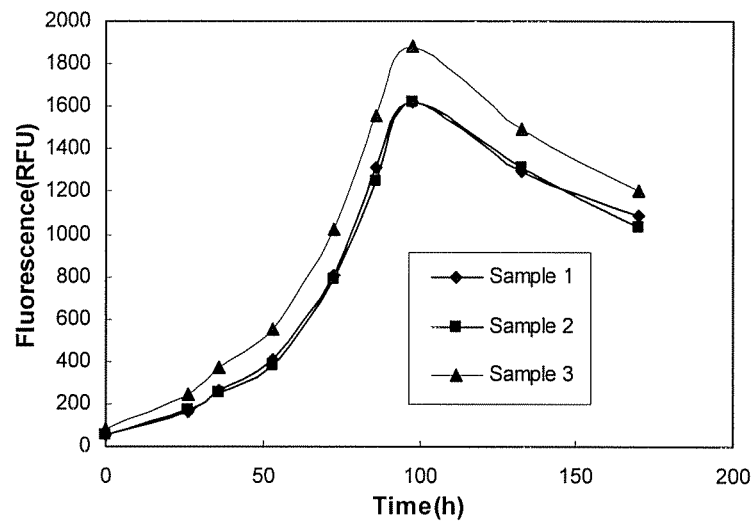
FIG. 6 illustrates cell growth kinetics as monitored by fluorescence signals. Batch kinetics of cell growth was monitored by fluorescence intensity for ES-GFP cultured in fabricated 96-well plate with PET matrices. The growth kinetics as monitored with the GFP fluorescence intensity were consistent in triplicate runs and could be used to determine the specific growth rate of the culture under culturing conditions.
Figure 20:
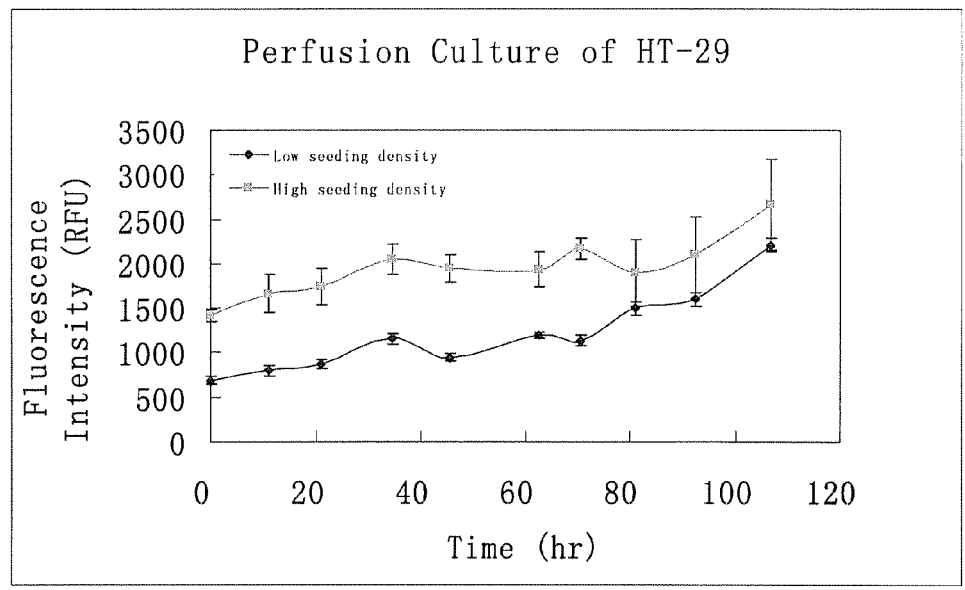
FIG. 20 illustrates perfusion culture of HT-29 expressing EGFP in the microfluidic bioreactor array for over 100 hours.

The design of the microfluidic bioreactor array had four inlets and one outlet (see FIG. 3C, D). Four 10 mL, syringes were autoclaved and filled with the maintenance media, which were then seated on a syringe pump (PHD 2000, Harvard Apparatus). PET fibrous scaffolds were seeded with low and high densities of cells (both were above $10^6$ cells/mL, though), and the device was packaged with the FAA method. The device was then connected to the four corresponding syringes on the pump, and a waste collector was connected at the other end of the device. This process was carried out in a cell culture hood aseptically. Then the bubbles within the microchip were driven out by infusion at a flow rate of 200 µL/min. The whole system was placed in a $CO_2$ cell culture incubator, and the perfusion was set at a rate of 0.7 µL/min. Cell proliferation was analyzed twice a day with the specific plate definition scheme in the microplate reader. The perfusion culture was maintained for about 5 days before the media were used up. As shown in FIG. 20, under the perfusion culture conditions, cells in the microbioreactors continued to grow as indicated by the increasing fluorescence intensity over 100 hours until the experiment was stopped when the media in the syringes were depleted. This showed that the perfusion culture microbioreactor system was able to sustain long term cell growth in the 3-D culture.

Effect of 5-FU on HT-29 Proliferation

Figure 21:
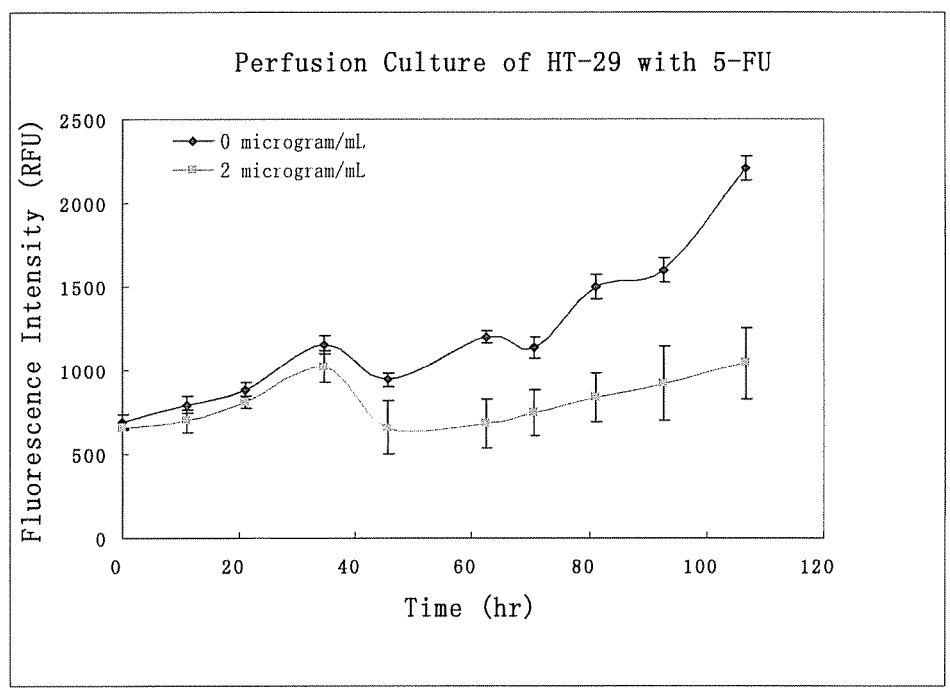
FIG. 21 illustrates the effect of 5-FU on the proliferation of HT-29 in perfusion culture with the microfluidic bioreactor array. In the presence of 5-FU at 2 μg/ml, cell proliferation was significantly inhibited as indicated by the much slower increase in the culture fluorescence.

The toxicity studies for 5-FU on the perfusion culture of HT-29 may be conducted with different dosing modes. One way is to feed the drug continuously at different concentrations in the media to different lines of culture (with controls) from the beginning of the perfusion to see the effects of the drug on actively proliferating cells in 3-D matrices. A second way is to first culture the cells without drug addition until highly dense tissues are formed and reach a stationary phase. Then the drug perfusion is initiated similarly to the first mode. Another mode is to feed the cells, either actively proliferating or in a stationary phase, intermittently with bolus administration to see how the cells respond to the drug. A drug test was performed with the first mode using 5-FU at 2 µg/mL, which significantly reduced cell proliferation as compared to the control without drug addition (FIG. 21). The microfluidic bioreactor thus can be used in the perfusion mode to evaluate cytotoxicity of drugs.

It will be obvious to those skilled in the art that various changes may be made without departing from the scope of the invention, which is not to be considered limited to what is described in the specification.

What is claimed is:

1. A device for performing dynamic cellular assays utilizing a microplate reader, the device comprising:
a plate having a plurality of vessels, each vessel having a bottom and at least one wall extending around said bottom to define a cavity operable to hold a fluid therein, the cavity having a first area and a second area, the first area and the second area lying on a common horizontal plane normal to a detected emission direction, and the second area is at least about three times larger than the first area;
a plurality of cell support structures, each cell support structure having a porosity operable to permit transmission of at least one form of radiant energy therethrough, and having a thickness operable to allow three-dimensional cell growth therein and to allow amplification of the radiant energy through tunneling therethrough,
wherein a cell support structure is anchored in the first area of the cavity of each vessel such that when the cavity is filled or substantially filled with a fluid, the fluid contacts the cell support structure in the first area of the cavity and the second area of the cavity is substantially occupied by the fluid;
wherein an emission from cells in the cell support structure is intensified in and can be read from the first area of the cavity;
wherein a noise signal resulting substantially from the fluid can be read from the second area of the cavity, the noise signal useful for performing noise correction of the emission read from the first area of the cavity.

2. The device according to claim 1, wherein the cell support structure has a thickness of about 1 mm.

3. The device according to claim 1, wherein the cell support structure has a porosity of about 85%.

4. The device according to claim 1, wherein the cell support structure is a scaffold.

5. The device according to claim 4, wherein the scaffold is non-woven.

6. The device according to claim 4, wherein the scaffold is formed of one or a combination of natural and synthetic fibers.

7. The device according to claim 6, wherein the scaffold is a fibrous material.

8. The device according to claim 7, wherein the scaffold is polyethylene terephthalate.

9. The device according to claim 1, comprising a means for anchoring the cell support structure in the cavity of the vessel.

10. The device according to claim 9, wherein the means for anchoring is one of an adhesive mechanical attachment and a mechanical restraint.

11. The device according to claim 1, wherein the cell support structure is anchored proximate to the bottom of the vessel.

12. The device according to claim 1, wherein the vessel wall is substantially elliptical.

13. The device according to claim 1, wherein the vessel comprises four walls arranged at right angles to one another.

14. The device according to claim 1, further comprising a first port and a second port, wherein the vessels are in fluid communication and the first port is in fluid communication with at least one vessel and the second port is in fluid communication with at least one vessel such that the fluid can flow through the vessels from the first port to the second port.

15. A method for analyzing cellular function of cells in three-dimensional culture, the method comprising:
    seeding at least one cell support structure with at least one cell, the cell support structure having a porosity operable to permit transmission of at least one form of radiant energy therethrough, and having a thickness operable to allow three-dimensional cell growth therein,
    providing a plate having a plurality of vessels, each vessel having a bottom and at least one wall extending around said bottom to define a cavity operable to hold a fluid therein, the cavity having a first area and a second area, the first area and the second area lying on a common horizontal plane normal to a detected emission direction, and the second area is at least about three times larger than the first area,
    anchoring a cell support structure in the first area of the cavity of each vessel;
    disposing a fluid in each vessel to culture the at least one cell such that the first area of the cavity is substantially occupied by the cell support structure and the fluid, and the second area of the cavity is substantially occupied by the fluid;
    detecting an emission from the culture in the first area of the cavity with a microplate reader;
    detecting a noise signal from the fluid in the second area of the cavity with the microplate reader; and
    using the noise signal to perform noise correction of the emission.

16. The method according to claim 15, further comprising treating the culture with one or more test conditions such that a change in the culture is detectible using at least one of radiation emitting, light transmission, fluorometric, and colorimetric assays.

17. The method according to claim 16, wherein the treatment includes introduction of one or a combination of conditions or agents that may have a therapeutic or toxic effect on the culture.

18. The method according to claim 16, wherein the treatment comprises addition of a cytotoxic agent to the culture, by application to the cells within the cell support structure or introduction into the fluid.

19. The method according to claim 15, wherein the cell is selected from mammalian, avian, reptilian, microbial and insect cells.

20. The method according to claim 19, wherein the cell is selected from stem cells, cancer cells, Chinese hamster ovary cells and NIH 3T3 cells.

21. The method according to claim 20, wherein the stem cell is an embryonic stem cell and is engineered to express green fluorescent protein.

22. The method according to claim 21, wherein an assessment of an effect of a treatment is made by observing changes in culture fluorescence.

23. The method according to claim 22, wherein the fluid is pumped through the seeded cell support structure so as to provide flow of fluid through the vessel.

24. The method according to claim 15, wherein the cell is engineered to express a fluorescent protein such that the cell emits a fluorescent light that can be detected optically.

25. The method according to claim 24, wherein expression of the fluorescent protein is controlled by a CMV promoter such that intensity of the emitted fluorescent light is proportional to a cell density or number.

* * * * *